United States Patent [19]
Walters

[11] 4,049,004
[45] Sept. 20, 1977

[54] IMPLANTABLE DIGITAL CARDIAC PACER HAVING EXTERNALLY SELECTIBLE OPERATING PARAMETERS AND "ONE SHOT" DIGITAL PULSE GENERATOR FOR USE THEREIN

[75] Inventor: Robert A. Walters, Pittsburgh, Pa.

[73] Assignee: ARCO Medical Products Company, Leechburg, Pa.

[21] Appl. No.: 663,372

[22] Filed: Mar. 3, 1976

Related U.S. Application Data

[63] Continuation-in-part of Ser. No. 654,584, Feb. 2, 1976, which is a continuation-in-part of Ser. No. 625,295, Oct. 23, 1975, abandoned.

[51] Int. Cl.² ............................................. A61N 1/36
[52] U.S. Cl. ............................. 128/419 PG; 307/273
[58] Field of Search ......... 128/419 E, 419 P, 419 PG, 128/419 PT, 419 R, 421, 422, 423; 307/265, 273; 328/193

[56] References Cited

U.S. PATENT DOCUMENTS

| | | | |
|---|---|---|---|
| 3,557,796 | 1/1971 | Keller, Jr. et al. | 128/419 PG |
| 3,727,616 | 4/1973 | Lenzkes | 128/419 E |
| 3,805,796 | 4/1974 | Terry, Jr. et al. | 128/419 PG |
| 3,833,005 | 9/1974 | Wingrove | 128/419 PG |

Primary Examiner—William E. Kamm
Attorney, Agent, or Firm—Richard A. Bachand

[57] ABSTRACT

An implantable cardiac pacer is instructable to vary the stimulation pulse interval, the stimulation pulse width, the stimulation pulse amplitude, the pacer sensitivity, the refractory period and the mode (demand or asynchronous).

A master parameter control circuit is provided to vary selected parameters of the heart pacer in accordance with an externally applied control signal.

An external control unit produces two sequential series of pulses, the first series being an access comprising at least one digital "0" state which must be detected by an access code detecting circuit within the master parameter control before the following parameter code will be accepted to vary the pacer parameters. The parameter code, generated subsequently to the access code, determines the selected set of pacer parameters, and can be selected from external controls upon the external control unit.

The master parameter control circuit includes means for recognizing the access code to enable the master parameter control circuit to only thereafter accept the selected parameter code. The entire parameter code must then be entirely received prior to changing the pacer parameters.

24 Claims, 12 Drawing Figures

IMPLANTABLE DIGITAL CARDIAC PACER HAVING EXTERNALLY SELECTIBLE OPERATING PARAMETERS AND "ONE SHOT" DIGITAL PULSE GENERATOR FOR USE THEREIN

CROSS REFERENCE TO RELATED APPLICATIONS

This application is a contnuation-in-part of application Ser. No. 654,504, filed Feb. 2, 1976, which is a continuation-in-part of application Ser. No. 625,295, filed Oct. 23, 1975, now abandoned.

BACKGROUND OF THE INVENTION

1. Field of the Invention

This invention relates to heart pacers, and more particularly to heart pacers of the type of which the operating parameters can be remotely varied and controlled.

2. Description of the Prior Art

Heart pacers are often provided with various means to control selected operating parameters so that, for example, the pacer can be adjusted to respond to and provide signals to a patient in accordance with his individual needs. After the pacer has been implanted, however, effecting changes in any particular operating parameter of the pacer may become a severe problem. Such changes are often necessitated, for instance, by an improvement or deterioration in the patient's condition which may require certain adjustments, for instance, that rate at which stimulation pulses are provided to the patient, the pulse width and amplitude of the pulses provided, the refractory period exhibited by the pacer, the sensitivity to naturally produced heart signals, and the operating mode of the pacer, such as demand mode, fixed rate mode, and the like.

In the past, there have been various proposals to effect changes in selected heart pacer parameters of an implanted heart pacer without major surgical intervention. For example, it has been proposed to provide a magnetic field responsive switch which can be activated by a magnet external to the patient, typically to change the pacer from a demand mode to a fixed rate mode. Additionally, pacers have been proposed which provide receptacles for receiving engaging surgical needles which can be inserted into the patient for adjustment of, for example, the value of a resistor or the like.

Implantable cardiac pacers have been advanced in the prior art which have certain operating parameters which can be adjusted without physically invading the user's body. Some prior art pacers typically include first and second digital pulse counters. The first counter receives a first predetermined set of input pulses, after which it produces an enabling signal to direct subsequent input pulses to the second counter. The second counter includes a plurality of outputs to activate various switches, each in parallel, for example, with a respective resistor in a plurality of series connected resistors to thereby control the input current to a transistor of a multivibrator to modify its time constant. Another output of the second counter controls a switch which bypasses a portion of the driving current to the output amplifier of the pacer to thereby control its output current.

Such prior art circuit, as above described, typically responds to an access code, which may be merely a sequential series of, for instance, seven or more consecutive pulses. One requirement of such circuit, however, is that seven access code pulses appear in a series to enable the first counter to count them. Thus, for example, if the wearer of a cardiac pacer embodying such circuit were to become exposed to a field to which the circuit responds, the circuit may erroneously detect the field pulses as the access code, and more importantly, thereafter reset the various parameters controlled by the circuit.

Additionally, prior art parameter adjustment circuits typically provide means for modifying the pulse rate only (and incidentally the width) and output current produced by the pacer, with no consideration given to many of the other important pacer parameters above mentioned.

One other disadvantage of prior art parameter adjustment circuts is that once the access pulses have been counted and the second counter is enabled, the data pulses applied to it produce immediate changes in the various output lines. These changes may undesirably produce immediate changes in the selection of the various timing resistors during the time while the data is still being received.

SUMMARY OF THE INVENTION

In light of the above, it is, therefore, an object of the invention to provide a digital cardiac pacer including means external to or remote from the pacer for controllably varying selected operating parameters of the pacer.

It is still another object of the invention to provide a digital cardiac pacer which can be, after implantation, externally to the user, controlled to vary any selected one or ones of the following operating parameters; the stimulation pulse width, the stimulation pulse amplitude, the demand or fixed rate modes stimulation pulse rate, the refractory period, the heart signal sensitivity, and the mode.

It is another object of the invention to provide a digital cardiac pacer which includes a memory for retaining pacer operating parameter determining signals which can be completely loaded into the memory prior to their execution.

It is still another object of the invention to provide a digital cardiac pacer and means for controllably varying the operating parameters thereof including a unique access code recognition circuit to assure that the operating parameter determining signals are not inadvertently recoded.

It is another object of the invention to provide a circuit for use in a digital cardiac pacer for controlling the sensitivity to heart frequency signals.

It is another object of the invention to provide a digital cardiac pacer in which the operating parameters can be independently varied.

It is another object of the invention to provide a one shot digital pulse generator for use in a heart pacer of the type which receives externally transmitted pules to produce a pulse of controlled amplitude and width upon the reception of an externally transmitted pulse.

These and other objects, features, and advantages will become apparent to those skilled in the art from the following detailed description when read in conjunction with the accompanying drawings and appended claims.

The invention, in a broad aspect thereof, presents an implantable digital cardiac pacer having externally selectible operating parameters. The pacer includes an external instruction device adapted to transmit a train of parameter selection pulses. The pacer includes means for receiving the train of pulses and generating a digital signal in response to the train. Memory means are included within the pacer for storing the digital signal, and means interconnect the pulse receiving means and the memory means to control the loading of the digital signal into the memory means. Means are also provided for varying at least one of the operating parameters of the pacer, and means connect the memory means and the parameter varying means to enable to the parameter varying means to control the at least one operating parameter in response to the digital signal generated. In another aspect of the invention, an implantable heart pacer includes externally controllable means for varying selected operating parameters, including the sensitivity, the refractory period, the stimulation pulse amplitude, the stimulation pulse width, the stimulation pulse rate, and the operating mode, i.e., fixed rate or demand.

Also included is a digital "one shot" pulse generator incorporating first and second triggerable flip-flops interconnected by a digital counter which controls the width of the pulse generated by the digital one shot generator.

In one embodiment of the invention, means are provided for detecting an externally access code, which includes a digital signal including at least one zero logic state to enable a subsequently transmitted series of data pulses to be received for controlling the operating parameters of the pacer.

BRIEF DESCRIPTION OF THE DRAWING

The invention as illustrated in the accompanying drawing, wherein.

In the various figures of the drawing, like reference numerals are used to denote like parts. Additionally, interconnections between the various circuits of the drawing are denoted by corresponding letters (A, B, C etc.).

DETAILED DESCRIPTION OF THE PREFERRED EMBODIMENTS

Figure 1:
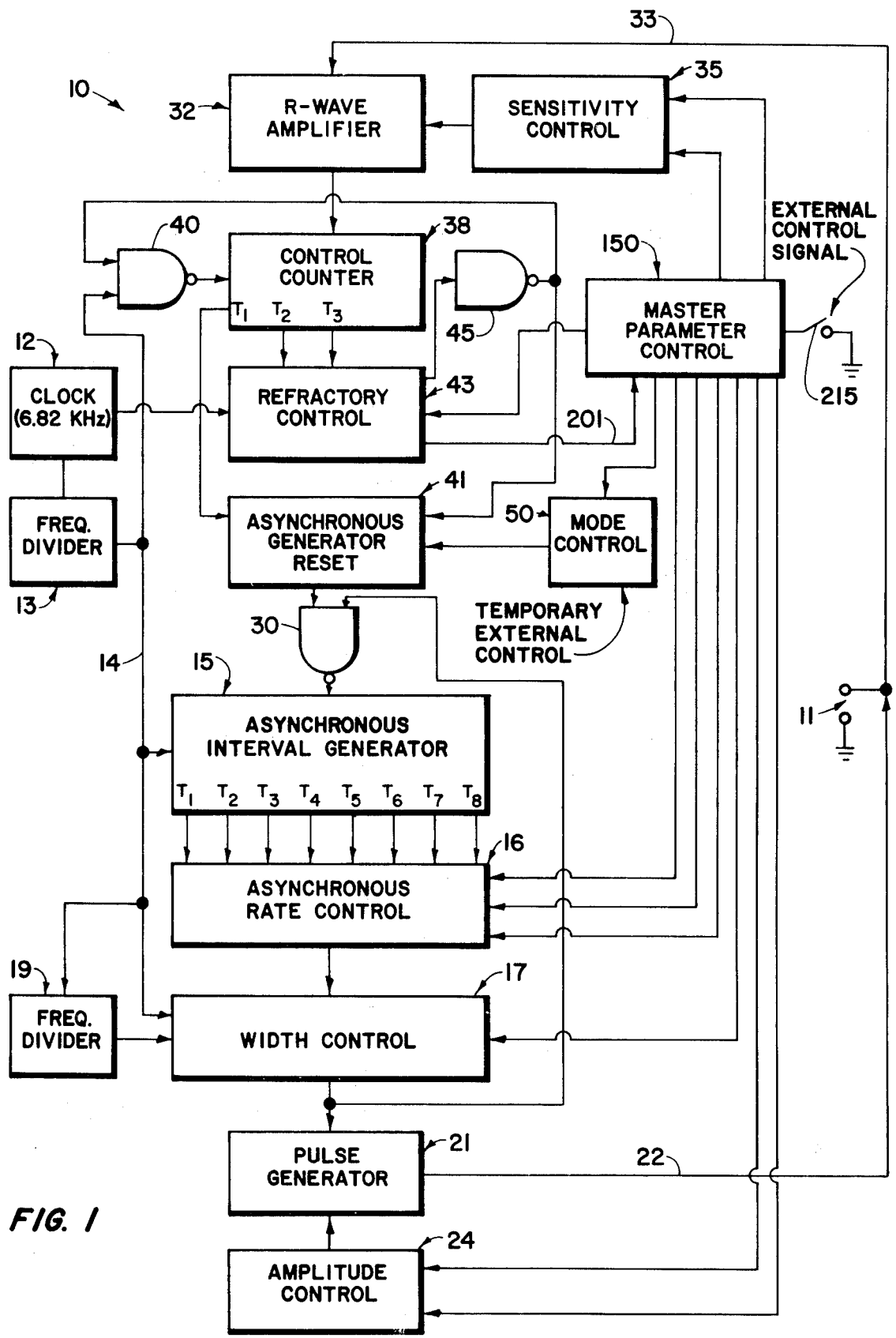
FIG. 1 is a box diagram of a heart pacer, in accordance with the invention, having various controllable parameters.

The cardiac pacer 10, in accordance with a preferred embodiment of the invention is shown in box diagram form in FIG. 1. (The various electrical circuits of the cardiac pacer in FIG. 1 ar illustrated and described below in detail with particular reference to FIGS. 2-5B).

With general reference to FIG. 1, the cardiac pacer 10 receives naturally produced cardiac and other signals from and supplies stimulation signals to a terminal 11, adapted to be connected to heart electrodes, such connections being well known in the art.

The cardiac pacer 10 operates in conjunction with a digital clock 12, which supplies clock pulses at a frequency of, for example, 6.82 KHz. Pulses from the clock 12 are divided by a frequency divider 13 to be supplied on line 14 to an asynchronous interval generator 15, having a plurality of outputs T1-T8, conducted to an asynchronous rate control circuit 16. Each of the outputs T1-T8 represents a different asynchronous interval within the range of interest, and the synchronous rate control 16 selects one of the outputs T1-T8 from the asynchronous interval generator 15, as controlled by a master parameter control 150.

The selected output from the asynchronous interval generator 15 is conducted to a width control circuit 17, which produces an output pulse of selected width as controlled by the master parameter control 150. This capability is enabled by the clock pulses upon the line 14 being applied directly to the width control 17, and to a frequency divider 19, which produces additional clock pulses at a submultiple of the frequency of the clock 12, for applicaton to the width control circuit 17, thereby providing signals from which the various widths of the output pulse can be selected.

The output pulses from the width control circuit 17 are applied to trigger a pulse 21 to produce an output pulse upon output line 22 for delivery to the heart terminals 11. The amplitude of the pulse generated by the pulse generator 21 is controlled by an amplitude control circuit 24, which, in turn, is also controlled by the master parameter control circuit 150.

The output of the width control circuit 17, in addition to its connection to the pulse generator 21, is conducted via a NAND gate 30 to a resetting terminal of the asynchronous interval generator 15. Thus, upon the reaching of a predetermined selected count of the asynchronous generator 15, upon the production of an output pulse from the width control circuit 17, the asynchronous interval generator is reset to begin counting a subsequent asynchronous interval.

The portion of the cardiac pacer thus described serves as a so-called fixed rate pacer, producing pulses asynchronously at a rate controlled by the selected output of the asynchronous interval generator 15. To provide a demand pacer capability, an R-wave amplifier 32 is provided. The heart terminals 11 are connected via line 33 to an input of the R-wave amplifier 32 to conduct naturally occurring heart pulses to the R-wave amplifier 32. Other signals, such as stimulation pulses produced by the pulse generator 21 upon the line 22, and electromagnetic interferring noise as may be detected by the heart electrodes or other associated circuitry may also be detected upon the line 33, but are filtered or rejected or initiate a interference or fixed rate mode, as will become apparent below. The sensitivity of the R-wave amplifier 32 is controlled by a sensitivity control circuit 35, which, in turn, is controlled by the master parameter control 150.

The R-wave amplifier 32 produces an output signal upon the detection of a naturally produced R-wave, a stimulation pulse, or an interference signal, for delivery to a control counter 38. The control counter 38 also receives clock pulses from the clock 12 via a NAND gate 40, and produces outputs at times $T_1$, $T_2$ and $T_3$, respectively after being reset. The output generated at time $T_1$ is conducted to an asynchronous generator reset circuit 41 which produces an output delivered via NAND gate 30 to reset the count of the asynchronous interval generator 15. Thus, in operation, if an R-wave, a stimulation pulse, or an interference signal is received by the R-wave amplifier 32 prior to the time which a signal appears on a selected output of the asynchronous interval generator 15, the asynchronous interval generator 15 is reset to begin its count anew, in a fashion known in the art as demand operation.

In addition, one or the other of the outputs $T_2$ or $T_3$ of the control counter is selected by a refractory control circuit 43, as controlled by the master parameter circuit 150. The selected output is conducted to an inverting NAND gate 45, for application to the NAND gate 40 controlling the passage of the clock pulses upon the line 14, and to the asynchronous generator reset circuit 41 to produce a state therein allowing the passage of a subsequently produced asynchronous generator reset pulse from the control counter 38. Thus, the refractory circuit functions to produce an "alert state" within the asynchronous generator reset circuit 41 after the control counter 38 has reached a predetermined refractory count determined by the refractory control circuit 43. Upon producing the alert state, a logic state is applied to the input of the NAND gate 40 disabling the passage of the clock pulses upon the line 14, terminating the counting by the control counter 38. Thereafter, the production of an output by the R-wave amplifier 32 produces a pulse resetting the control counter 38 and enabling it to begin its count again. When the count has reached time $T_1$, the asynchronous generator reset 41, previously enabled by the refractory control circuit 43, produces a reset pulses to reset the count of the asynchronous interval generator 15. Prior to the reaching of the "alert state," however, the pacer is in a "control state" during which the reception of a signal from the R-wave amplifier 32 does not produce an asynchronous interval generator resetting pulse, but instead the control counter 38 is merely reset to count the preselected refractory period from the beginning.

In addition, a mode control circuit 50 is provided which is controlled by the master parameter control 150. The mode control circuit 50, which operated, disables the operation of the asynchronous generator reset circuit 41, to thereby cause the pacer circuit 10 to operate in a fixed rate mode. Additionally, the mode control 50 can be operated by a temporary external control, such as an electromagnet or the like, to cause the circuit to operate in a fixed rate mode for testing purposes, as is well known in the art.

The master parameter control 150, below described in detail, is programmed via an external control signal applied to a receiving element 215, such as a magnetically activated reed switch or the like, as below described.

As indicated, the cardiac pacer 10, in accordance with the present invention, includes a facility for varying its operating parameters; more particularly, the stimulation pulse width, the stimulation pulse amplitude, the refractory period, the heart signal sensitivity, and the mode (i.e. fixed rate or demand) and the asynchronous pulse generation rate. These operating parameters, furthermore, can be varied after the pacer has been emplanted into the body of the patient. To facilitate this parameter controlability, the master parameter control circuit 150 is employed. The master parameter control circuit 150 is shown in box diagram form in FIG. 2, and in detail in FIGS. 3A-3C.

As will become apparent, the master parameter control circuit 150 is responsive to an externally applied input from an instruction device as below described. The instruction device provides an initial access sequence of electromagnetic pulses followed by a sequence of electromagnetic pulses for determining the operating parameters of the pacer. The control circuit 150 must first recognize the access sequence before the control sequence will be accepted and loaded into the control circuit memory. More particularly, with reference now to FIG. 2, the externally applied input signal is received and applied to a digital one shot pulse generator 151, which provides an output pulse of controlled amplitude and width for each externally applied input pulse to overcome problems associated with bounce of the signal input detection switch (described below). The output from the digital one shot generator 151 is applied to a start latch circuit 152 and a NAND gate 156. The output of the NAND gate 156 is conducted to the input of a shift register 165, the various outputs of which are connected to a pattern recognition circuit 172.

Concurrently, clock pulses from the clock 12 are applied to the digital one shot generator 151, a reset circuit 155 and a counter 162. Three outputs of the counter 162 which occur at various different times are conducted to the shift register 165, a pattern search stop latch 166, and a stop circuit 167. Additionally, the output from the NAND gate 156 is conducted into an input of the shift register 165, as well as to a second NAND gate 170.

An output from the pattern recognition circuit 172, as well as an output from the pattern search stop latch 166 are inputted to a NAND gate 174. The output of the NAND gate 174 is conducted to the input of an enable latch 176, and the output of the enable latch 176 is conducted to another input of the NAND gate 170 and to an AND gate 180. The output of the stop latch 167 is conducted to another input of the AND gate 180 and to a reset terminal of the start latch 152. The output of the NAND gate 170 is conducted to the input of a data counter 182, and the outputs of the data counter 182 are conducted to a data storage memory circuit 184. The output of the AND gate 180 is connected to a "store" terminal of the data storage memory circuit 184.

Briefly, in operation, upon the application of the externally applied input to the digital one shot pulse generator 151, the start latch 152 is activated. The start latch 152 activates the reset circuit 155 which initializes the shift register 165, the pattern search stop latch 166, the enable latch 176, the stop latch 167, and the data counter 182. Additionally, the activation of the start latch 152 permits the counter 162 to begin its count. The counter 162, as will be below described in detail, produces outputs which are submultiples of the clock frequency.

The data from the digital one shot pulse generator is then applied via NAND gate 156 (enabled to pass the data because of the output of the start latch 152) to the pattern recognition shift register 165. The first seven data bits are clocked into the shift register 165 at a submultiple frequency of the clock 160 (1/32 thereof in the embodiment illustrated). The data in the shift register 165 is continuously applied to the combinational logic pattern recognition circuit 172, which produces an output if and only if the pre-selected recognition code appears in the shift register 165. Concurrently, the pattern search stop latch 166 is activated by another output from the counter 162 at another submultiple of the frequency of the clock 160 (for example, 1/256 of the clock frequency, the time required to clock the first seven data bits into the shift register 165). The output from the pattern search stop latch 166, when applied together with the output from the pattern recognition circuitry 172 to the NAND gate 174 activates the enable latch 176. The data appearing at the output of the NAND gate 156, therefore, is applied by the NAND gate 170 to the data counter 182, thence to the data storage circuit 184.

At a time at which the data is completely loaded into the data storage 184, the stop latch 167 is activated to produce a signal which is applied to a store terminal of the data storage circuit 184 via AND gate 180. Concurrently, the output from the stop latch 167 is applied to the start latch 152 to reset it to an initial condition to preclude further transmission of data into the circuit 150.

At this point, the data from the external instruction device is stored in the data storage circuit 184 for changing the operating parameters of the pacer circuit.

Figure 2:
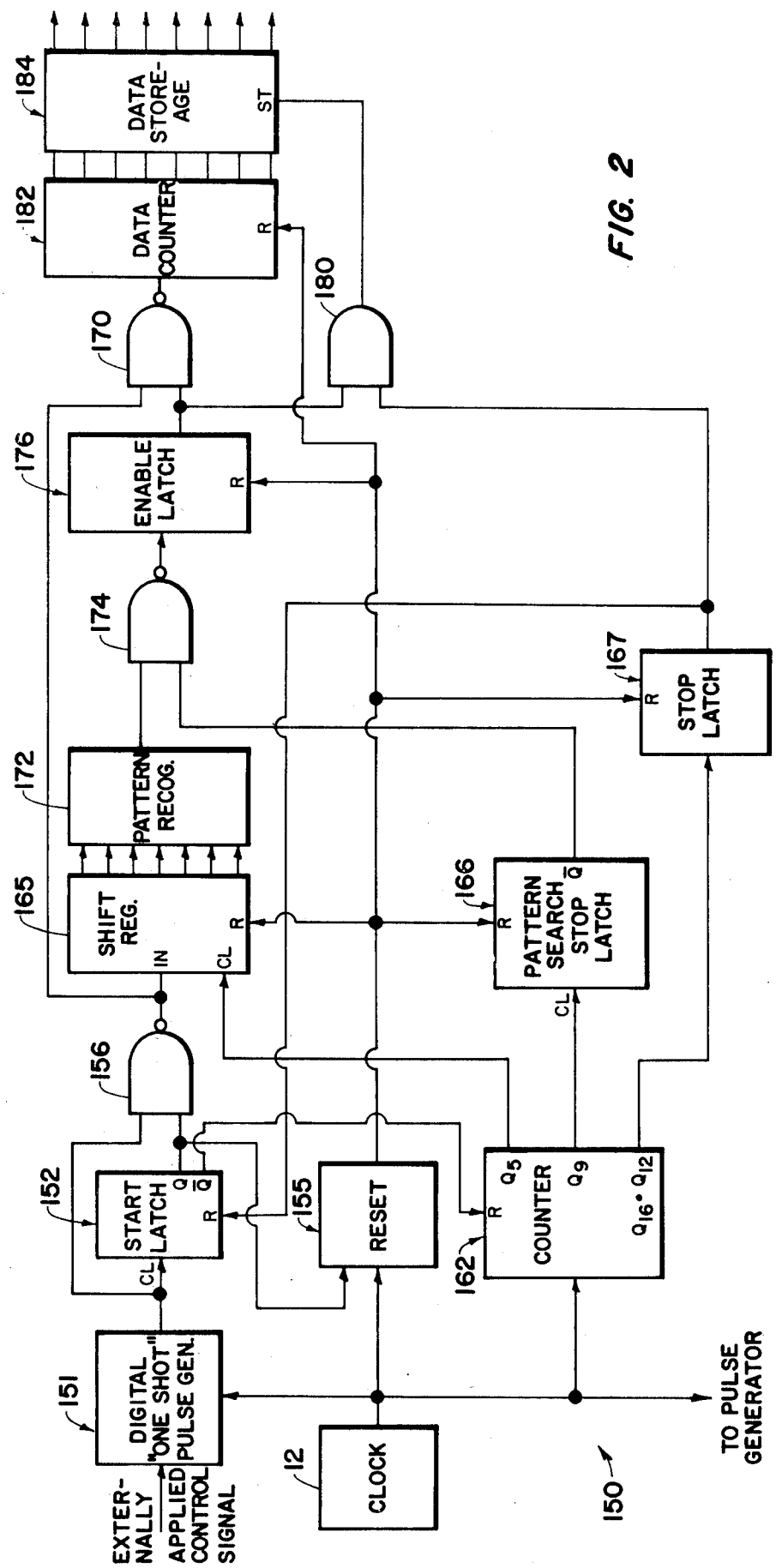
FIG. 2 is a box diagram illustrating the circuitry of the master parameter control circuit, including the access code recognition circuitry, the instruction memory, and the circuitry for loading the instruction code into the memory, in accordance with one aspect of the invention.
Figure 3A:
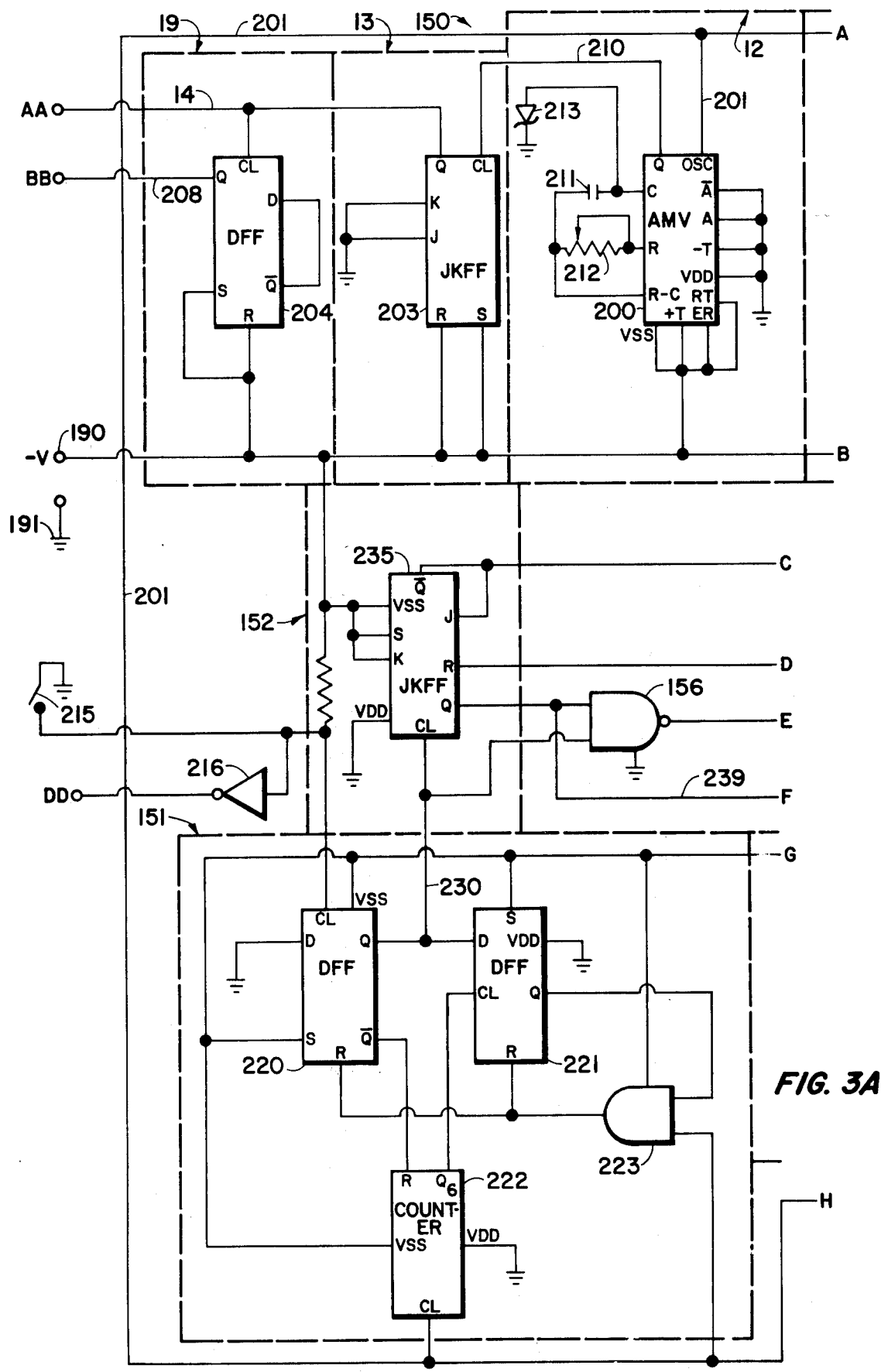
FIGS. 3A, 3B and 3C are a detailed electrical schematic diagram of the master parameter control circuit of FIG. 2.
Figure 3B:
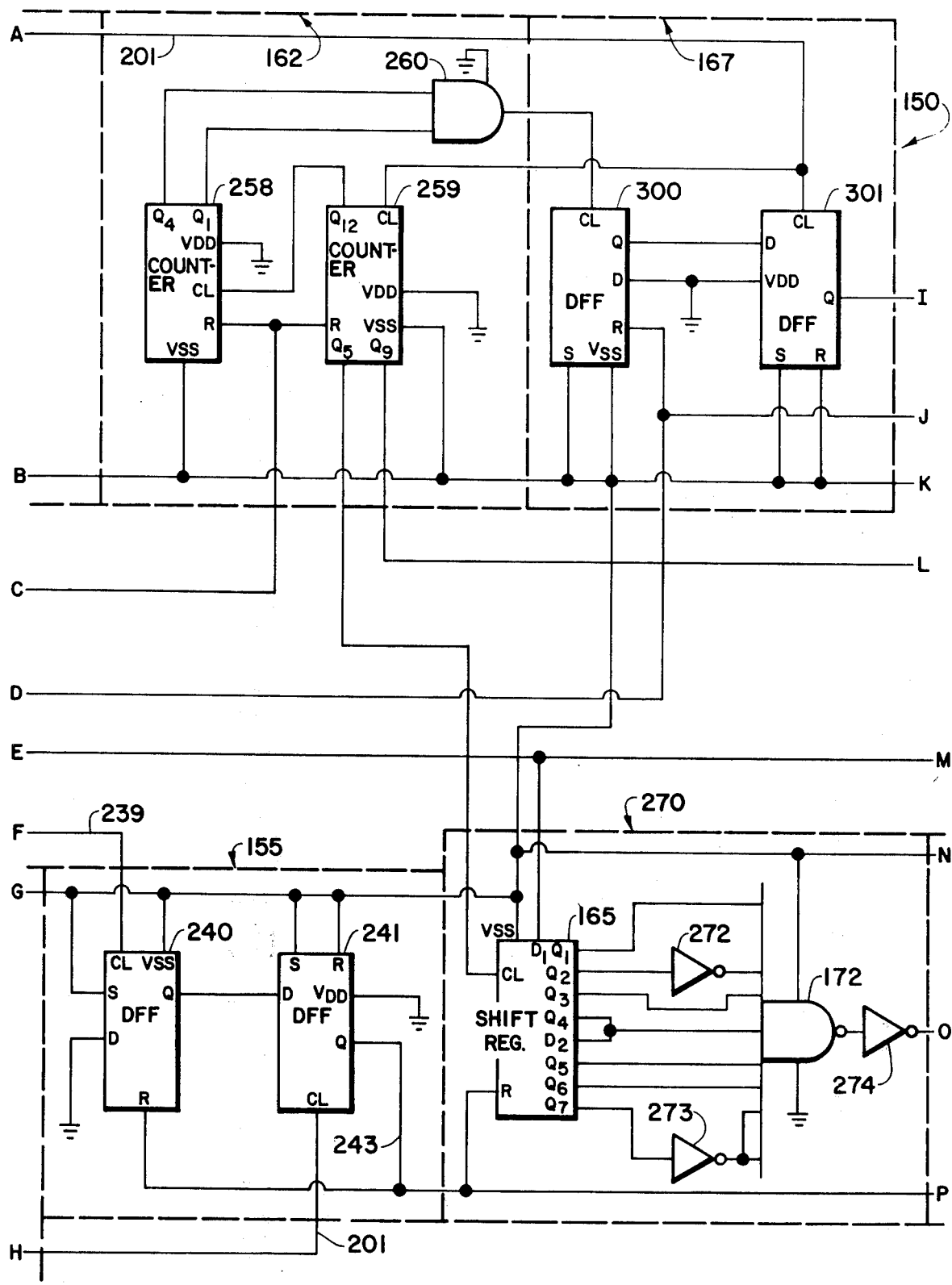
Figure 3C:
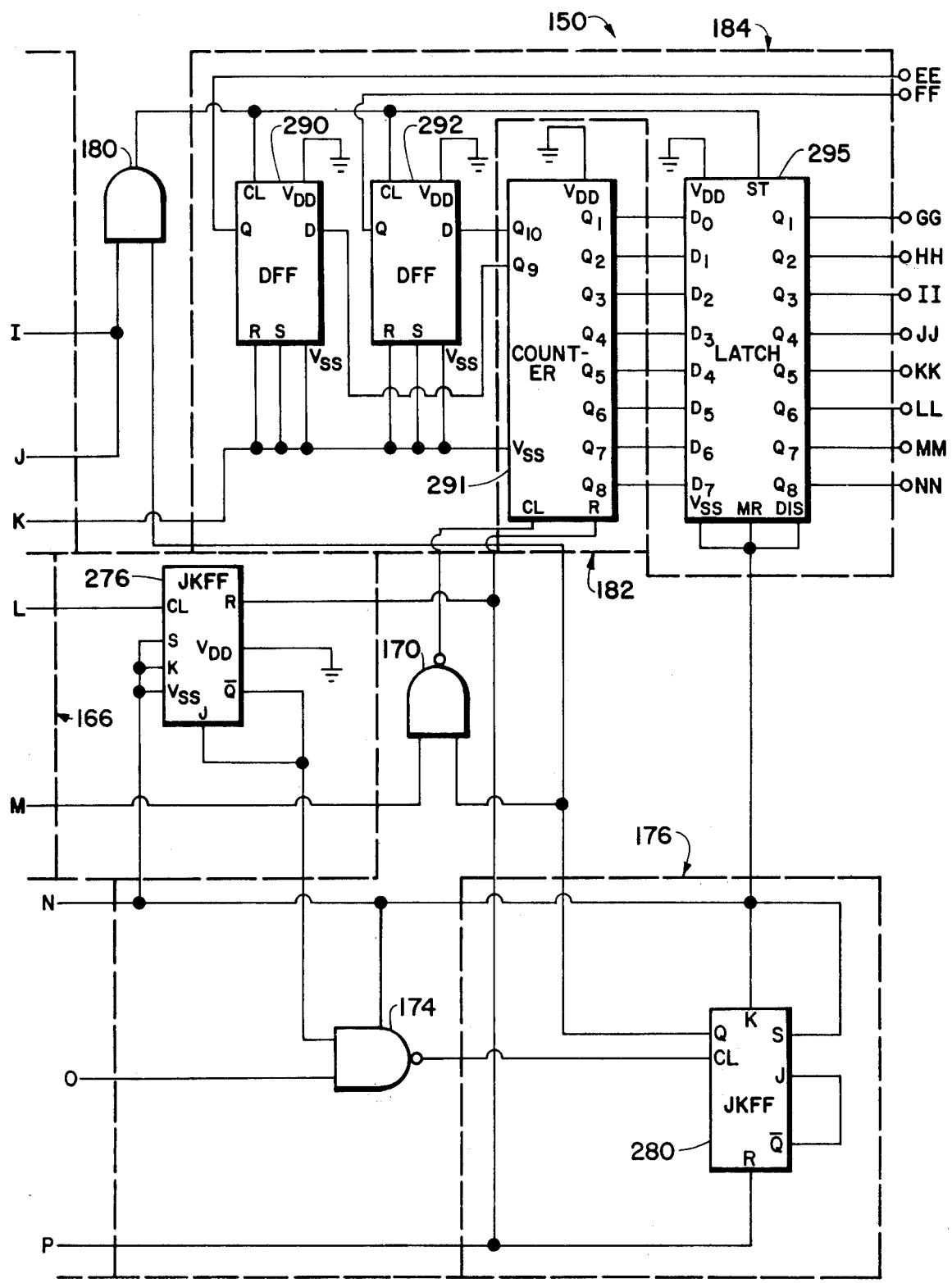

The control pulse receiving circuit of FIG. 2 is shown in greater detail in FIGS. 3A-3C. More particularly, the clock 12 (FIG. 3A) includes an astable multivibrator 200 which provides an oscillator output upon line 201 to supply clock pulses to the remainder of the circuit. A frequency divider circuit 13 is also provided, including a J-K master-slave flip-flop 203 to which a divided frequency output from the astable multivibrator 200 is applied to the clock input thereof; and a D-type flip-flop 204 to which the Q output of the J-K flip-flop 203 is applied to a clock input thereof. The $\overline{Q}$ output of the flip-flop 204 is connected to the D input, whereby the output alternates between high and low states with successive clock pulses to divide the clock frequency by two. The output of the D flip-flop 204 is conducted from the circuit on line 208 (the connection continuing from point BB to the width control circuit 17, FIG. 5B). Since the Q output of the astable multivibrator 200 is at one-half of the oscillation frequency generated, the output from the D flip-flop 204 will be the clock frequency divided by four. The set and reset terminals of the D flip-flop 204 and the J-K flip-flop 203 are connected to a low state 190 to assure the continuous operation of the respective flip-flops.

The $V_{ss}$, the positive trigger, the external reset, and the retrigger terminals of the clock 200 are tied low; and the astable, negative trigger and the $V_{dd}$ are tied high. The integrated circuit 200, therefore, operates as an astable multivibrator with the output thereof appearing on line 201, and a one-half submultiple frequency appearing on line 210, applied to the flip-flop 203, as above indicated. Thus, the output on line 201 is the primary clock frequency; the output on line 14 (point AA) is the first divided of the primary clock frequency established by the divider circuit 13; and the output on line 208 (point BB) is the second divided clock frequency, established by the divider circuit 19. The frequency of the clock 12 is determined by the values of the capacitor 211 and resistor 212 connected between the capacitor and resistor terminals, respectively, and the R-C common terminal of the astable multivibrator 200. The frequency can be adjusted by varying the value of the resistance of the resistor 212. In the embodiment illustrated, the resistor is about 2MΩ, and the capacitor is about 100 pf; consequently, the clock frequency can be adjusted to be about 6.82KHz. A zener diode 213 is connected between the capacitor terminal of the multivibrator 200 and ground, to cause the oscillator frequency to decrease with decreasing battery voltage.

The data from the external instruction device (below described) is received by a magnetically actuated reed switch 215 and is conducted to the digital one shot generator 151 (FIG. 3A). The pulse generator 151 assures that the pulse received from the reed switch 215 is of proper shape and width for handling by the remainder of the circuitry, and includes two D-type flip-flops 220 and 221, a ripple-carry binary counter 222, and an AND gate 223. The data is applied to the clock input of the D flip-flop 220, the D input of which is tied high. The output Q of the flip-flop 220 is connected to the D input of the D flip-flop 221, and the Q output of the D flip-flop 221 is conducted through the AND gate 223 to the reset terminals of the flip-flops 220 and 221. The primary clock pulses appearing on line 201 are additionally applied to the AND gate 223 to synchronize the resetting of the D flip-flops 220 and 221. The $\overline{Q}$ output of the D flip-flop 220 is applied to a reset terminal of the counter 222. The clock terminal of the counter 222 is connected to the line 201 to receive primary clock pulses therefrom. The output of the counter 222 is taken at, for example, output $Q_6$ and applied to the clock terminal of the D flip-flop 221.

Thus, when a data pulse is received from the switch 215, it serves to clock the high state on the D terminal to the Q output, thence to the D input of the flip-flop 221. As the Q output goes high, the $\overline{Q}$ output goes low, thereby removing the high reset state from the counter 222, enabling it to begin counting the clock pulses applied thereto upon line 201. When the output line $Q_6$ goes high (in $2^6$ times the clock frequency divided by two, seconds), the high state on the D input of the flip-flop 221 will be clocked through to the Q output thereof to be applied to an input of the AND gate 223. Upon the occurrence of the next clock pulse on line 201, the high state will be applied to the reset terminals of the flip-flops 220 and 221 to return them to their initial states. Thus, the pulse appearing on output line 230 will be of constant width, that being estblished by the time for the output $Q_6$ of the counter 222 to assume a high state from the time the pulse is received from switch 215. The amplitude of the output pulse on line 230 will, of course, be constant, equal to that of the high state.

The output from the digital one shot generator is applied to the start latch circuit 152 (FIG. 3A). The start latch circuit 152 includes a J-K master-slave flip-flop 235 to the clock input of which the output from the digital one shot generator 151 is applied. The K input of the flip-flop 235 is tied low, and the J input is connected to the $\overline{Q}$ output. The Q output, therefore, is high continuously after the reception of the first clock pulse, until the flip-flop 235 is reset. The reset terminal is connected to the stop latch circuit 167 (FIG. 3B), below described. The Q output of the flip-flop 235 is applied to one input terminal of a NAND gate 156, and the data generated upon the output line 230 of the pulse generator 151 is applied to the other input terminal. The output of the NAND gate 156 is applied to the shift register 165 (FIG. 3B) and to one input terminal of the NAND gate 170 (FIG. 3C) for transmission to the data counter 182 (FIG. 3C), as described below.

The Q output of the J-K flip-flop 235 is applied to the reset circuit 155 (FIG. 3B), which includes two D-type flip-flops 240 and 241. The D input of the flip-flop 240 is tied high, and the output upon line 239 from the start latch circuit is connected to the clock input. Thus, when the state upon line 239 changes from low to high, the high state upon the D input is transferred to the Q output of the flip-flop 240 to appear upon the D input to the flip-flop 241. The clock terminal of the flip-flop 241 is connected to receive primary clock pulses appearing upon the line 201. Thus, upon activation of the start latch 235, the high state upon the D input of the flip-flop 240 is transferred through, with the occurrence of a clock pulse, to the Q output of the flip-flop 241, to present a high resetting state upon the output line 243, which is connected to the reset terminals of the flip-flop 240, the shift register 165, the enable latch 176 (FIG. 3C), the pattern search stop latch 166 (FIG. 3C), and the data counter 182 (FIG. 3C), as below described. The reset pulse, however, is of self-limiting duration, being terminated upon its appearance at the reset terminal of the flip-flop 240 after the occurrence of a subsequent primary clock pulse upon line 201.

The $\overline{Q}$ output of the start latch flip-flop 235 (FIG. 3A) is applied to the reset terminals of the counter circuits of the counter 162 (FIG. 3B). The counter 162 includes a ripple-carry binary counter 258, a ripple-carry binary counter 259 and an AND gate 260. Both the counters 258 and 259 are reset by the $\overline{Q}$ output of the start latch flip-flop 235. Thus, when the start latch 235 is activated, the reset state normally appearing on the reset terminals 258 and 259 is removed, initiating the count of the counter 162.

The primary clock pulses upon line 201 are connected to the clock input of the counter 259, and the outputs developed upon lines $Q_5$, $Q_9$ and $Q_{12}$ are conducted to the shift register 165 (FIG. 3B), the pattern search stop latch 166 (FIG. 3C), and the clock terminal of the counter 258, respectively. Thus, the outputs from the counter 259 occur at submultiples of the clock frequency appearing upon line 201; for example, since the clock frequency is about 6.82KHz (having a period of about 0.1466 milliseconds), the pulses upon line $Q_5$ are of period of approximately 4.69 milliseconds, the outputs on line $Q_9$ are of period approximately 75.07 milliseconds, and the outputs on line $Q_{12}$ are of period approximately 600.58 milliseconds.

The output from output terminal $Q_1$ of the counter 258 is connected to one terminal of the AND gate 260 and the output from line $Q_4$ is connected to the other input thereof. Since the counter 258 receives its clock pulses from the $Q_{12}$ output of the counter 259, the outputs $Q_1$ and $Q_4$ of the counter 258 at the output of the AND gate 260 will change from low to high states in period of about 5,405.28 milliseconds. As will become apparent, the data received upon the switch 215 will be received at a frequency period appearing on output terminal $Q_5$ of the counter 259, or 4.69 milliseconds. Therefore, the change in state at the output of the AND gate 260 will be 1152 data pulses after the counters are permitted to begin their count, to activate the stop latch circuit 167 (FIG. 3B), below described.

In its operation, the circuit first seeks an access code pattern of pulses received by the input switch 215. For this purpose, a pattern recognition circuit 270 (FIG. 3B) is provided, including a shift register 165 and a pattern recognizing NAND gate 172. The output $Q_5$ of the counter 259 is applied to the clock input of the shift register 165. The data produced by the one shot pulse generator 151 (FIG. 3A) is applied via NAND gate 156 to the "data" input of the shift register 165. The data is clocked into the shift register 165 at the frequency of the pulses generated upon the terminal $Q_5$ of the counter 259. Thus, it can be seen that if the pulses transmitted to the circuit are not at the frequency produced upon the line $Q_5$ of the counter 259, the data will not be properly clocked into the shift register 165, and will not be recognized by the pattern recognition circuit 172 below described. This clocking requirement therefore imposes a frequency constraint upon the input data in addition to the other requirements (especially the pattern of high and low states) thereby increasing the statistical odds against inadvertent actuation of the parameter determining code circuitry.

As the data is shifted into the shift register 165, it appears as the output terminals $Q_1$, $Q_2$, $Q_3$, $Q_4$, $Q_5$, $Q_6$, and $Q_7$. The output terminals of the shift register 165 are connected to the input terminals of the NAND gate 172. If desired, various ones of the output lines of the shift register 165 can be inverted, such as by inverters 272 and 273, to thereby provide a facility of uniquely coding the required recognition pattern to the circuit.

The NAND gate 172 produces a low output only upon the concurrence of all of the inputs thereto. Thus, only at the time when the outputs of the shift register 165 correspond to the predetermined access code will they produce a state change at the output terminal of the NAND gate 172. The output at the NAND gate 172 is inverted by an inverter 274 to be applied to an input of the NAND gate 174 (FIG. 3C).

After a sufficient time for the access pattern to be recognized, the circuit is disabled from continuing its access pattern search by the pattern search stop latch 166 (FIG. 3C). The pattern search stop latch 166 includes a J-K master-slave flip-flop 276 which receives its clock input from the output $Q_9$ of the counter 259. The K input of the flip-flop 276 is tied low, and the J input is tied to the $\overline{Q}$ output. Thus, upon the reception of a clock pulse upon the clock terminal, the $\overline{Q}$ output will change from a normally low to a high state, where it will remain until the flip-flop 276 is reset. The $\overline{Q}$ output is connected to the other terminal of the NAND gate 174 to prevent further transmission of signals from the pattern recognition circuit 270 therethrough. Since the clock input to the flip-flop 276 is derived from the output terminal $Q_9$ of the flip-flop 259, the pattern search stop latch will be activated approximately 37.55 milliseconds after the start latch 152 has been activated. This corresponds to a period which includes eight data bits transmitted at the rate determined by the output $Q_5$ of the counter 259. Thus, once the access pattern search is begun, if it is not recognized within the first eight pulses, the circuit will discontinue its search and not accept further data until the time required for an entire programming cycle has elapsed.

Immediately prior to the activation of the pattern search stop latch 166, if the access pattern is recognized, the output from the pattern recognition circuit 270 is applied through the NAND gate 174 to the enable latch circuit 176 (FIG. 3C), which includes a J-K masterslave flip-flop 280. The flip-flop 280 has its K input tied low and the $\overline{Q}$ output tied to the J input. The signal from the pattern recognition circuit is applied to the clock input. Thus, once the enable pulse pattern is recognized, the enable latch produces a high state output upon the Q output terminal thereof, which will continue until reset. The Q output terminal of the flip-flop 280 is connected to one input of the NAND gate 170 to control the transmission of the data transmitted through the gate 156 (FIG. 3C). The Q output of the flip-flop 280 is additionally connected to an input of the AND gate 180 to be compared with the output of the stop latch circuit 167 (FIG. 3B), below described. Thus, once the enable latch 176 changes state upon the recognition of the access pattern, the data upon the line 230 is applied to the data counter circuit 182 (FIG. 3C).

The data counter 182 includes a ripple-carry counter 291. The data from the one shot pulse generator 151 (FIG. 3A) is applied to the clock input of the counter 291. Thus, as the data is entered into the counter 291, the output states $Q_1$-$Q_{10}$ will reflect the number of pulses received. It should be noted that the output produced on the terminals $Q_1$-$Q_{10}$ is the binary equivalent to the number of pulses received at the clock input, with the most significant digit being located upon the line $Q_{10}$.

The data upon lines $Q_1$-$Q_{10}$ of the counter 291 are connected directly to the data storage circuit 184 (FIG. 3C). The data storage circuit 184 includes a latch 295 and two D-type flip-flops 290 and 292 for storing the signals applied thereto. The various outputs $Q_1$-$Q_8$ of the counter 291 are applied to the various data inputs of the latch 295, the store terminals of which are connected to the output of the AND gate 180, which, as above described, receives its inputs from the outputs of the stop latch circuit 167 (FIG. 3B) and the enable latch circuit 176 (FIG. 3C). The $Q_9$ and $Q_{10}$ outputs of the counter 291 are connected to the respective D inputs of flip-flops 290 and 292, respectively. The Q outputs of the flip-flops 290 and 292 constitute two additional control data states at points EE and FF.

The stop latch circuit 167 (FIG. 3B) includes two D-type flip-flops 300 and 301. The primary clock pulses upon the line 201 are connected to the clock input of the flip-flop 301, and as above indicated, the $Q_1$ and $Q_4$ outputs of the counter 258 are conducted through the AND gate 260 to the clock input of the other flip-flop 300. The D input of the flip-flop 300 is connected high, and the Q output is connected to the D input of the flip-flop 301. The Q output of the flip-flop 301 is connected to one of the input terminals of the AND gate 180 and to the reset terminal of the flip-flop 300.

Thus, when all of the data which has been received by the circuit within the time period defined by the change in concurrence of state changes of the outputs $Q_1$ and $Q_4$ of the counter 258 is received, the stop latch circuit 167 and the enable latch circuit 176 (FIG. 3C) will produce a signal to the store terminals of the latch 295 (FIG. 3C) to thereby enter the data appearing at the data terminal inputs thereof. The data will then be thereafter stored in the latch circuit until another signal set, including a proper access code, is subsequently applied to the circuit. The outputs appearing upon the latch 295 are, thereafter, available for conduction to various modification circuits to change the operating parameters of the heart pacer with which the circuit is employed.

Figure 4:
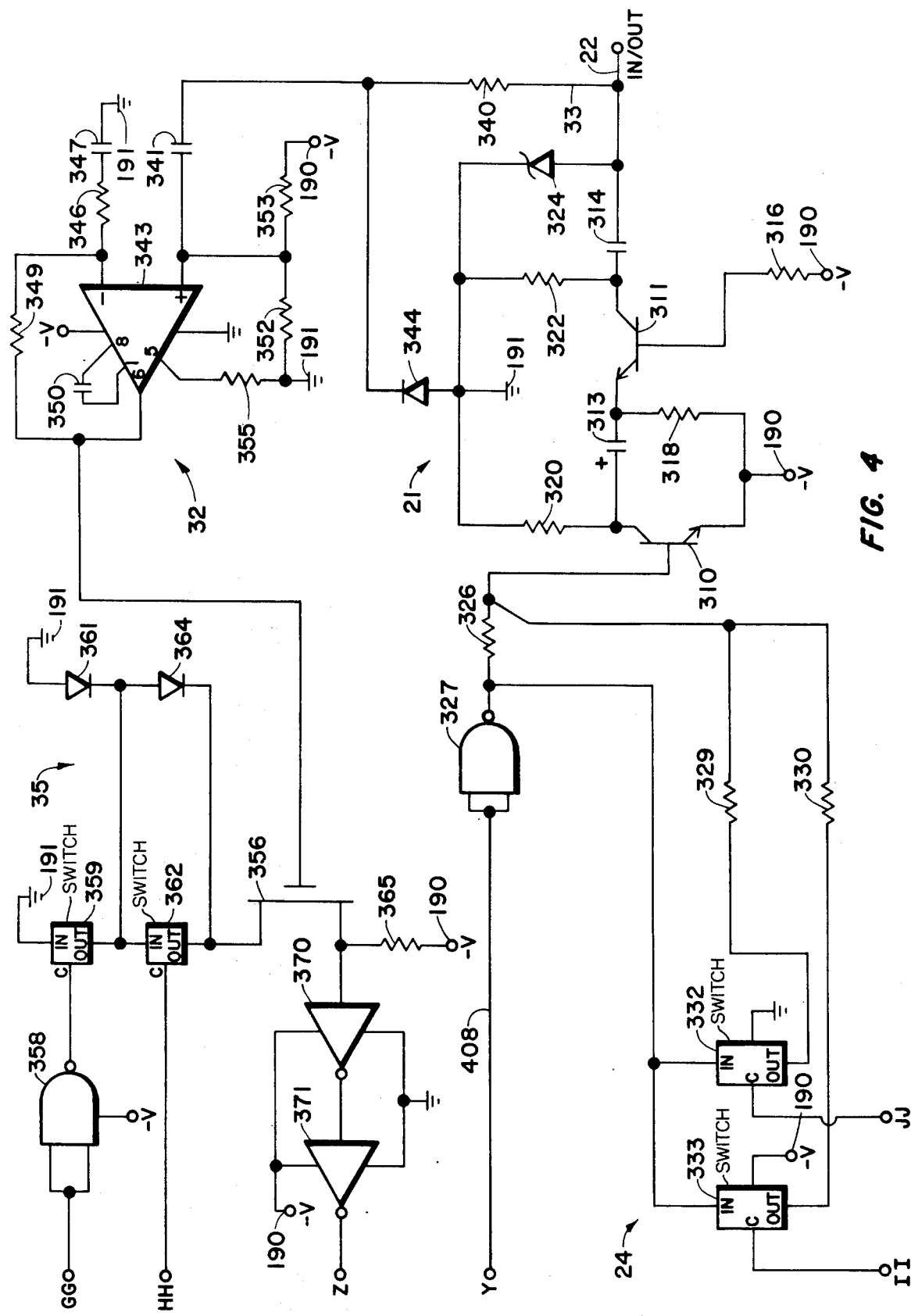
FIG. 4 is a detailed electrical schematic diagram of the pulse generator and amplitude control circuits and of the R-wave amplifier and sensitivity control circuts of the cardiac pacer of FIG. 1.

The electrical schematic diagram of the pulse generator 21 (See FIG. 1) is shown in detail in FIG. 4. The pulse generator 21 functions as a voltage multiplying circuit, and includes two n-p-n transistors 310 and 311. The collector and emitter of the transistor 311 interconnect one side of a capacitor 313 in series with the output line 22 via a capacitor 314. A resistor 316 connects the base of the transistor 311 to a negative terminal 190 and a resistor 322 connects the collector of the transistor 311 to a ground terminal 191, to reverse bias the collector-base junction of the transistor 311.

The side of the capacitor 313 which is connected to the emitter of the transistor 311 is also connected to a negative potential at terminal 190 by a resistor 318. The opposite plate of the capacitor 313 is connected to the collector of the transistor 310 and to a ground potential 191 by a resistor 320. The emitter of the transistor 310 is connected directly to the negative terminal 190. Thus, when the transistors 310 and 311 in their normally non-conducting states, the capacitor 313 becomes charged, as indicated, by the voltage between the negative terminal 190 and the ground terminal 191 through resistors 318 and 320.

When the transistor 310 is biased into condition, as below described, the negative potential upon its emitter is connected in series with the previously charged capacitor 313, thereby multiplying the voltage developed between the emitter of the transistor 311 with respect to ground. Additionally, this increased negative potential forward biases the base-emitter junction of the transistor 311, causing it to conduct, delivering the multiplied voltage to the output line 22, as above described.

A zener diode 324 is connected between the output line 22 and ground 191 to protect against defibrillation and other undesirably high voltages which may be encountered.

The production of the stimulation pulse, as above indicated, is controlled by the application of a base current to the transistor 310. This base current is established in a resistive path in series between the base of the transistor 310 and the output of a NAND gate 327. The inputs to the NAND gate 327 are interconnected so that the NAND gate inverts the signal derived from the output of the width control circuit 17 (see FIG. 1), as below described in detail.

The resistance of the resistive path, and, consequently, the base current of the transistor 310 is controlled by an amplitude control circuit 24. The amplitude control circuit 24 includes three resistors 326, 329, ad 330. The resistors 329 and 330 are connected in parallel with each other and with the resistor 326 by bilateral switches 332 and 333, respectively. The switches 332 and 333 receive digital operating signals upon lines II and JJ, respectively, which are derived at the output of the data storage circuit 295 in the master parameter control 150 (see FIG. 3C). Thus, in operation, the presence of a logic 00 upon the respective terminals II and JJ results in the entire value of the resistor 326 being presented to control the base current of the transistor 310. The presence of a logic 01 upon the terminals II and JJ will cause the switch 332 to close to result in the resistive value of the parallel combination of the resistors 329 and 326 in the base circuit. The presence of the logic value 10 upon the terminals II and JJ will result switch 333 closing to produce the parallel combination of the resistors 330 and 326 in the base circuit. And the presence of a logic 11 upon the terminals II and JJ will result in both switches 332 and 333 closing to produce the parallel combination of all three resistors 329, 330, and 326 in the base circuit. Thus, the collector-emitter current of the transistor 310 is controlled by the logic value presented upon the terminals II and JJ.

The amount the transistor 310 is biased into conduction, as controlled by the logic state upon the terminals II and JJ, determines the amplitude of the output pulse delivered to the output line 22. That is, the voltage drop between the collector and emitter determines the voltage which is seen in series with the voltage previously impressed upon the capacitor 313.

The output line 22, which, in addition to delivering stimulation pulses from the pulse generator 21, as above described, serves to conduct naturally produced heart pulses to the detection portion of the pacer 10 upon line 33. A resistor 340 is connected in series with a capacitor 341 to a non-inverting input of an operational amplifier 343. The resistor 340 and the capacitor 341, in addition to coupling the signal to the input, serve as a low frequency filter, the capacitor 341 presenting a high impedance to the low frequency components of the detected signal upon the line 22. A diode 344 is connected from between the resistor 340 and the capacitor 341 to a ground terminal 191, to clamp the amplitude of the stimulation pulse to an acceptable voltage, to prevent overloading the amplifier 343.

A resistor 346 is connected in series with a capacitor 347 between a ground terminal 191 and an inverting input to the operational amplifier 343. A feedback resistor 349 is connected between the output of the amplifier 343 and its inverting input. The resistor 346 and the capacitor 347 also serve as a low frequency filter to the signal produced at the output of the operational amplifier 343. A feed-forward compensation capacitor 350 is provided for determining the high 3db frequency roll-off point. Finally, the non-inverting input of the amplifier 343 is connected to a voltage divider comprising two resistors 352 and 353 connected in series between a negative terminal 190 and a ground terminal 191. An offset balance resistor 355 is connected between the ground terminal 191 and an offset balance terminal of the amplifier 343. The output of the amplifier 343 is connected to the gate of an FET transistor 356 to control the source-drain current therethrough. Thus, upon the reception of a naturally produced heart pulse (or other signal having similar frequency characteristics), the amplifier 343 produces an output voltage to turn on the FET 356. The extent to which the FET 356 is turned on is, of course, dependent on the output voltage of the amplifier 343, which, in turn, is determined by the amplitude of the signal sensing upon the line 22.

The sensitivity of the pacer 10 to the signal produced by the R-wve amplifier 32 is controlled by the sensitivity control circuit 35 (see FIG. 1). The sensitivity control circuit 35 includes a NAND gate 358, the inputs of which are interconnected to the output terminals GG of the data storage latch 295 (see FIG. 3C) so that the NAND gate 358 inverts the signal thereat. The output from the NAND gate 358 is connected to a control terminal of a bilateral switch 359 which is connected in parallel with a Schottky diode 361.

Another terminal HH of the latch 295 (FIG. 3C) is connected to a second bilateral switch 362, which is connected in parallel with a silicon diode 364. Additionally, the anode of the diode 361 is connected to a ground terminal 191, and the cathode of the diode 364 is connected to the source of the FET 356. A resistor 365 is connected between the drain of the FET 356 and a negative terminal 190. Thus, a current path is defined from the ground terminal 191 through the diodes 361 and 364, the source and drain of the FET 356 and the resistor 365 to the negative terminal 190. Since the forward resistances of the Schottky and silicon diodes 361 and 364 are on the order of about 0.2 and 0.7 ohms, respectively, the current through the resistor 365 when the FET 356 is in a conducting state can be controlled by the operation of one or the other, neither or both of the bilateral switches 359 and 362. For example, if the logic level 00 were applied to the respective terminals GG and HH, the bilateral switch 359 is turned on and the bilateral switch 362 is turned off, to provide a current path from the ground terminal 191 through the switch 359 and diode 364 to the source of the FET 356. A logic level 01 on the terminals GG and HH turn both switches 359 and 362 on, bipassing both diodes 361 and 364 in the current path from the ground terminal 191 to the source. A logic level 10 on the respective terminals GG and HH turns the switch 359 off and the switch 362 off, providing a current path through both diodes 361 and 364 from the ground terminal 191 to the source. Finally, a logic level 11 on the input terminals GG and HH turns the switch 359 off and the switch 362 on, thereby providing a current path from the ground terminal 191 through the diode 361 and switch 362 to the source of the FET 356. Thus, by the application of the appropriate logic level to the terminals GG and HH, the potential applied to the source of the FET 356 can be controllably varied to determine the voltage level at which the FET 356 is turned on. When the FET 356 is turned on, a voltage is developed across the resistor 365, which is applied to an input of a pair of inverters 370 and 371 for application to the control counter 38 (see FIG. 1).

Figure 5A:
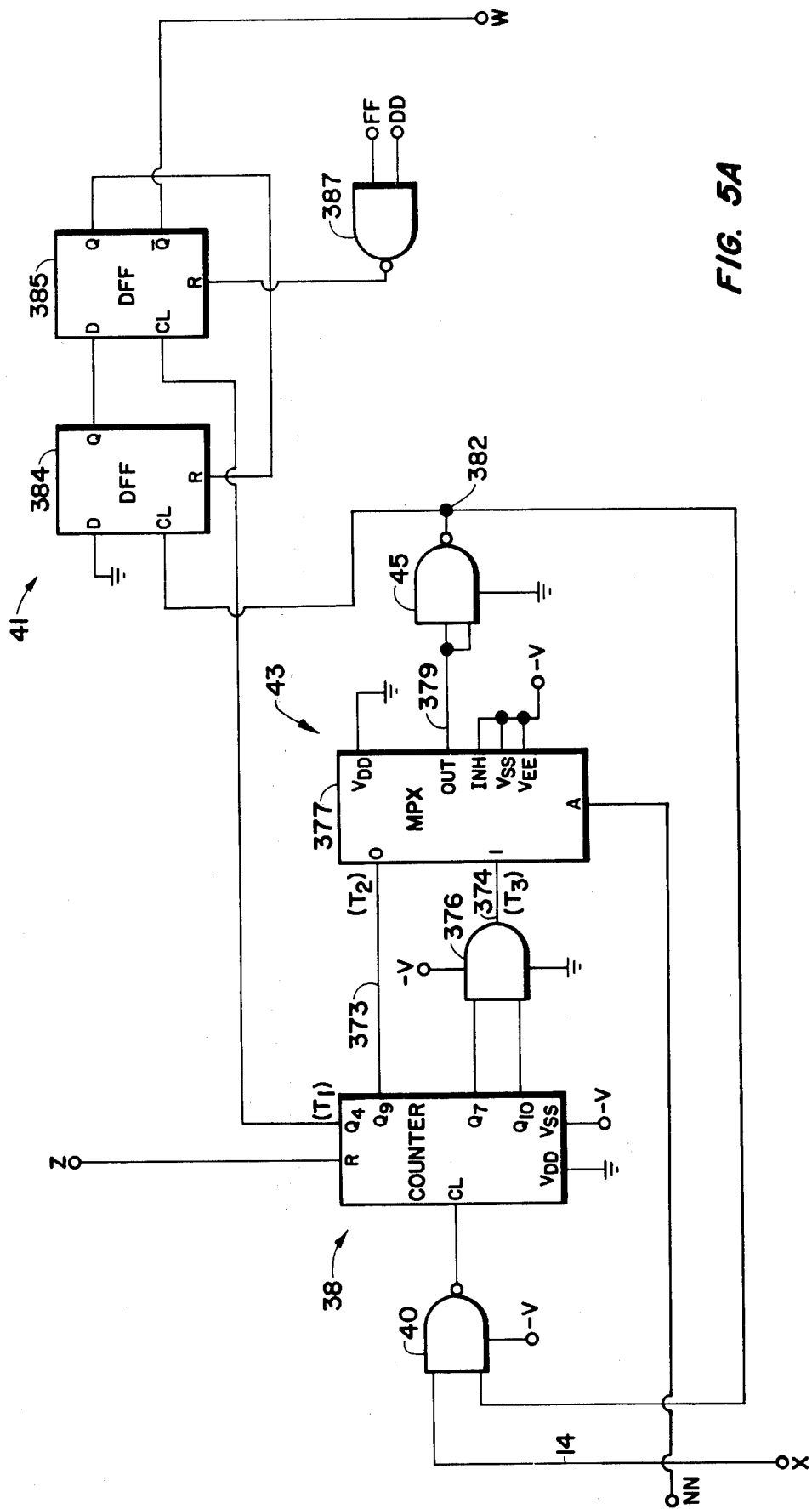
FIGS. 5A and 5B are a detailed electrical schematic diagram of the control counter circuit, refractory control circuits, asynchronous generator resetting circuit, mode control circuit, asynchronous interval generator circuit, asynchronous rate control circuit, and width control circuit of the cardiac pacer of FIG. 1.
Figure 5B:
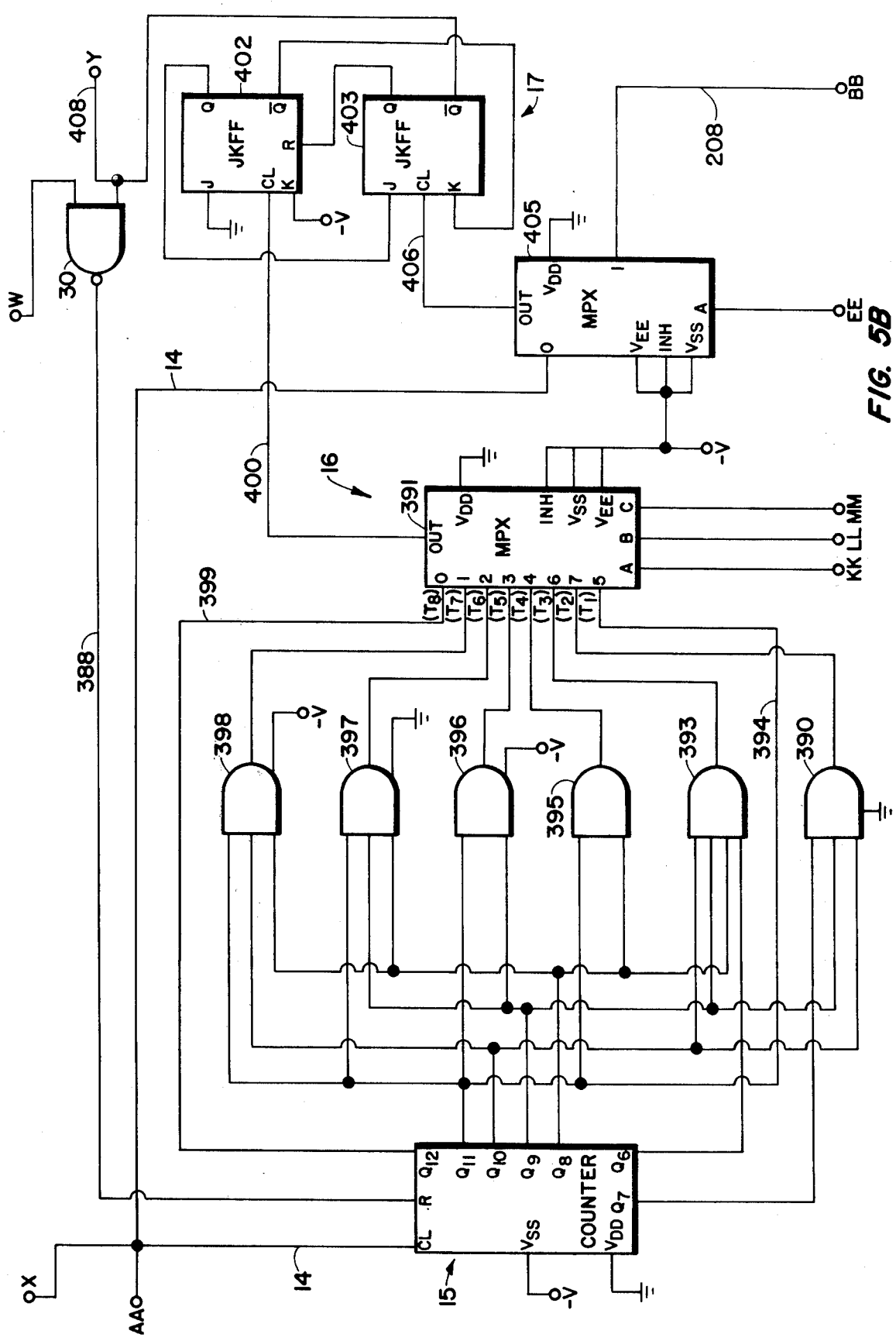

The control counter circuit 38, refractory control 43, asynchronous generator reset circuit 41, asynchronous interval generator 15, asynchronous rate control 16, and width control circuit 17 as set forth in FIG. 1 are shown in detail in FIGS. 5A and 5B. Pulses which represent first divided clock pulses at a one-fourth divided frequency from the primary clock pulses supplied by the clock 12 (see FIG. 3A) are conducted to the various circuit components upon line 14, as shown.

The output from the R-wave amplifier 32 is conducted by the line Z to the reset terminal of the control counter 38, as shown in FIG. 5A. Thus, upon the detection of an appropriate signal by the R-wave amplifier 32, a reset signal is applied to the control counter 38. First divided clock pulses upon the line 14 are conducted to one input of the NAND gate 40, the output of which is connected to the clock input of the counter 38. The counter 38, is a ripple carry counter, and produces outputs upon its various respective output terminals corresponding to a predetermined respective count of clock pulses applied to its clock terminal. The primary function of the control counter 38, as described briefly above, is to define a refractory state or control interval during which the reception of a naturally occurring heart pulse has no resetting effect, and after which the reception of such pulse produces a resetting pulse, indicating that the heart is properly functioning. There are two selectible output lines from the counter 38, one being taken upon the line 373 from the $Q_9$ output, and the other being taken upon the line 374, being taken from the $Q_7$ and the $Q_{10}$ outputs via a AND gate 376. The signals upon the lines 373 and 374 represent a change in state corresponding to clock pulses of $2^9 \div 2 = 256$ and $2^{10} + 2^7 \div 2 = 576$. The clock pulses upon line 14, being of approximately 0.587 milliseconds, produce changes in states upon the line 373 and 374 after 150.15 milliseconds and 337.83 milliseconds, respectively. Thus, a capability of choice between the respective times of changes in state upon the lines 373 and 374 to determine the refractory period of the pacer is made available. The selection between the signals upon the lines 373 and 374 is made by a multiplexer 377. The line 373 is connected to the O input and the line 374 is connected to the 1 input, respectively, of the multiplexer 377. The A input is connected to the terminal $Q_8$ (NN) of the latch 295 (FIG. 3C) to present the signal thereupon to the multiplxer 377. The truth table of the multiplexer 377 provides that upon the application of a zero state to the A terminal, the signal on the O input terminal is applied upon the output terminal to the line 379. A 1 state applied to the A terminal connects the signal upon the 1 input to the output line 379. Therefore, the signal presented upon the output $Q_8$ of the latch 295 (FIG. 3C) representing the refractory control signal determines whether the refractory period of the circuit is 150.14 milliseconds as determined by the signal on the line 373 or 337.83 milliseconds as determined by the signal on the line 374. The output from the multiplexer 377 upon the line 379 is conducted to an inverting NAND gate 45 the output of which is connected to the asynchronous generator reset circuit 41 and to one of the terminals of the NAND gate 40 at the input of the control counter 38. In operation, after the counter 38 is reset, it begins to count clock pulses applied to its clock input via the NAND gate 40. Upon reaching the predetermined count upon the selected output line 373 or 374, an output signal is generated upon the line 379 to the inverting NAND gate 45, producing a change in state upon the output line 382 from a normally high to a low state. Upon the change in state upon the line 382, the NAND gate 40 is disabled from passing additional clock pulses to the counter 38 thereby stopping its count. The control counter 38, therefore, is caused to discontinue its count until it is reset by a subsequently received pulse from the R-wave amplifier 32.

In addition to the outputs produced upon the terminals $Q_9$, $Q_7$ and $Q_{10}$, an output is produced upon the terminal $Q_4$ of the counter 38 which is conducted to the asynchronous generator reset circuit 41, as next immediately described.

The asynchronous generator reset circuit 41 includes two D-type flip-flops 384 and 385. The D input of the flip-flop 384 is connected to a high state, and the Q output thereof is connected to the D input of the flip-flop 385. The Q output of the flip-flop 85 is connected to the reset terminal of the flip-flop 384, and the $\overline{Q}$ output of the flip-flop 385 represents the output of the asynchronous generator reset circuit 41, to be conducted to one input of the NAND gate 30 (FIG. 5B). The output of the NAND gate 45 upon the line 382, representing the selected refractory period signal, is applied to the clock input of the flip-flop 384. The output upon the terminal $Q_4$ of the counter is applied to the clock input of the other flip-flop 385. Thus, in operation, after the control counter 38 is reset, it begins its count, reaching first a count to produce an output upon the terminal $Q_4$ to thereby clock the high state on the D input thereof through to the D input of the flip flop 385. When the counter 38 subsequently reaches the count on the selected output upon line 373 or line 374, a clock pulse is applied to the clock input of the flip-flop 385, thereby producing a change in state upon its outputs, the Q output changing from low to high states and the $\overline{Q}$ output changing from high to low states. The change in output from high to low states upon the $\overline{Q}$ output, applied to the NAND gate 30 (FIG. 5B), defines the reset signal for delivery to the asynchronous interval generator 15 (FIG. 5B).

Thus, it can be seen that if a reset signal is received upon the reset terminal of the counter 38 prior to its reaching the count on the selected output line 373 or 374, the counter is reset to begin its count completely anew, without producing an output pulse from the flip-flop 385. This resetting condition can be prolonged indefinitely, if, for example, an interference signal is caused to continually reset the counter 38 within the refractory period determined by the master parameter control 150. After the predeterined count has been reached, however, the flip-flop 385 having been previously "armed" by the signal upon the terminal $Q_4$ of the counter produces a reset signal upon the output terminal $\overline{Q}$ of the flip-flop 385.

At this point, it should be noted that the generation or not of a reset signal from the asynchronous generator reset circuit 41 controls the demand operation of the overall pacer circuit 10. Thus, for example, if no reset signal is generated, the asynchronous interval generator 15 is permitted to continuously count, producing stimulation signals at the predetermined selected rate.

A NAND gate 387 is provided, having its output connected to the reset terminal of the flip-flop 385. One input of the NAND gate 387 is connected to the inverter 216 (see FIG. 3A). The other input to the NAND gate 387 is connected to the output Q (FF) of the D-flip-flop 292 (FIG. 3C). Thus, if the reed switch 215 (FIG. 3A) is closed by, for example, the nearness of a magnet for testing purposes or the like, a high output state is produced by the NAND gate 387 to continuously supply a reset voltage to the flip-flop 385, to thereby disable the generation of resetting pulses, causing the pacer circuit 10 to operate asynchronously. Additionally, the presence of a 0 signal upon the output Q (FF) of the flip-flop 292 likewise produces a constant resetting voltage upon the output of the NAND gate 387, to constrain the pacer circuit 10 to asynchronous or fixed rate mode.

The resetting signal from the asynchronous generator reset circuit 41, delivered to the NAND gate 30, as above described, is delivered upon a line 388 to a resetting terminal of the asynchronous interval generator 15 (FIG. 5B). The asynchronous interval generator 15, which is of the ripple carry counter type, receives clock pulses upon line 14 to its clock terminal to produce outputs at various output terminals thereof. In the embodiment illustrated, for example, outputs are derived at terminals $Q_6$–$Q_{12}$. The output signals themselves are logic combinations of selected outputs, the selection of one of which can be employed to determine the asynchronous interval rate of the pacer circuit 10. More particularly, outputs from the $Q_7$, $Q_9$ and $Q_{10}$ terminals of the counter 15 are combined by an AND gate 390 to produce a change in output state after about 489.41 milliseconds. The output from the AND gate 390 is conducted to input 7 of a multiplexer 391. The outputs upon terminals $Q_6$, $Q_8$, $Q_9$ and $Q_{10}$ are combined by an AND gate 393 to produce a change in output state after approximately 544.29 milliseconds. The output from the AND gate 393 is connected to input terminal 6 of the multiplxer 391. The output terminal $Q_{11}$ of the counter 15 is connected directly by line 394 to input 5 of the multiplexer 391, and presents a signal which changes states after approximately 600.58 milliseconds. The output terminals $Q_8$ and $Q_{11}$ are combined by an AND gate 395, the output of which is connected to input terminal 4 of the multiplexer 391, and which produces a change in state after approximately 675.66 milliseconds. The output terminals $Q_9$ and $Q_{11}$ are combined in the AND gate 396, the output of which is connected to input terminal 3 of the multiplexer 391 to produce a change in state after about 750.73 milliseconds. The terminals $Q_8$, $Q_9$ and $Q_{11}$ are combined in the AND gate 397, the output of which is connected to input terminal 2 of the multiplexer 391 and produces a change in state after about 825.81 milliseconds. The terminals $Q_8$, $Q_{10}$ and $Q_{11}$ are combined in an AND gate 398, the output of which is connected to terminal 1 of the multiplexer 391 and which produces a change in state after about 975.96 milliseconds. Finally, output terminal $Q_{12}$ is connected directly to input terminal 0 of the multiplexer 391 on line 399, which produces a change in state after about 1201.17 milliseconds.

The control terminals A, B, and C of the multiplexer 391 are connected to three respective rate control terminals $Q_5$, $Q_6$ and $Q_7$ (KK, LL, MM) of the latch 295 (see FIG. 3C). The control signals which determine which of the inputs 0–7 is connected to the output line 400, is in accordance with the truth table below set forth:

| A | B | C | OUT |
|---|---|---|-----|
| 0 | 0 | 0 | 0 |
| 0 | 0 | 1 | 1 |
| 0 | 1 | 0 | 2 |
| 0 | 1 | 1 | 3 |
| 1 | 0 | 0 | 4 |
| 1 | 0 | 1 | 5 |
| 1 | 1 | 0 | 6 |
| 1 | 1 | 1 | 7 |

Thus, the output time upon one of the various multiplexer lines is selected by a logic input to the input terminals of the multiplexer, and, therefore, the asynchronous rate of the pacer circuit 10 can be selected among any of the above set forth various times.

The output signal upon the line 400 from the multiplexer 391 is conducted to the width control circuit 17, as follows. The width control circuit 17 includes two J-K masterslave flip-flops 402 and 403. The J input of the flip-flop 402 is connected high, and the K input is connected low. The Q and $\overline{Q}$ outputs of the flip-flop 402 are connected respectively to the J and K inputs of the flip-flop 403. The Q output of the flip-flop 403 is connected to the reset terminal of the flip-flop 402, and the $\overline{Q}$ output of the flip-flop 403 constitutes the output of the width control circuit 17. The signal upon the line 400 from the multiplexer 391 constitutes the clock signal to the flip-flop 402, which, upon its ocurrence, produces a high state upon the output Q and a low state upon the output $\overline{Q}$. The output from a width determining multiplexer circuit (below described) is connected to the clock input of the flip-flop 403 to clock the input upon the J-K terminals to the output terminals Q and $\overline{Q}$. More particularly, the multiplexer 405 receives first divided clock pulses upon the line 14 at its 0 input terminal. Additionally, it receives second divided clock pulses at a second divided frequency from the flip-flop 204 (FIG. 3A) upon line 208 (BB) at its 1 input terminal. The control terminal A receives its input from the width control signal at the Q output (EE) of the D-flip-flop 290 (FIG. 3C). Thus, depending on whether the signal upon the control terminal is high or low determines whether the clock pulses at the input terminals 0 or 1 are respectively applied to the output terminal upon the line 406 for delivery to the clock terminal of the flip-flop 403. It can be seen that the selection of the clock pulses at the lower frequency produces a longer change in state upon the output $\overline{Q}$ of the flip-flop 403 than the higher frequency of clock pulses upon the input line 0 of the multiplexer 405, thereby providing a facility for controlling the width of the pacer produced stimulation pulse. The output from the flip-flop 403 upon the $\overline{Q}$ output is conducted upon the line 408 to provide the drive signal to the pulse generator circuit 21 (FIGS. 1 and 4). The output upon the terminal $\overline{Q}$ of the flip-flop 403 is additionally conducted to one of the input of the NAND gate 30, to constitute an additional resetting signal to the asynchronous interval generator 15. Thus, upon the generation of an asynchronous signal, the asynchronous interval generator is reset to reinitiate its timing of its next subsequent asynchronous interval.

The external control unit, designated by the general reference numeral 500 for generating and transmitting the access code and the pulses for determining the parameters of the pacer 10, above described, is shown in detail in FIGS. 6A, 6B, 6C, and 6D. The connections between the figures are indicated by corresponding letters. As will become apparent, unlike the circuitry of the implantable pacer 10 above described with reference to FIGS. 1-5, the circuitry illustrated in FIGS. 6A–6D is configured with ground denoting a 0 or low logic state and $+v$ representing a high or 1 logic state.

The external control unit 500 includes four main sections, each encircled with dashed lines. An oscillator section 501 (FIG. 6B) provides clock pulses to the remainder of the external control unit circuitry. The access code generator 502 (FIG. 6B) generates a particular sequence of pulses for access into the master parameter control circuit 150 (FIGS. 1 and 3A-3C). A parameter code generator 503 (FIG. 6C) generates a controllable number of pulses, each number corresponding to an individual set of selectible pacer parameters. Finally, a pulse output circuit 504 (FIG. 6D) produces the electromagnetic pulses for transmission to the master parameter control in accordance with the access code generator 502 and the parameter code generated by the parameter code generator 503.

Figure 6A:
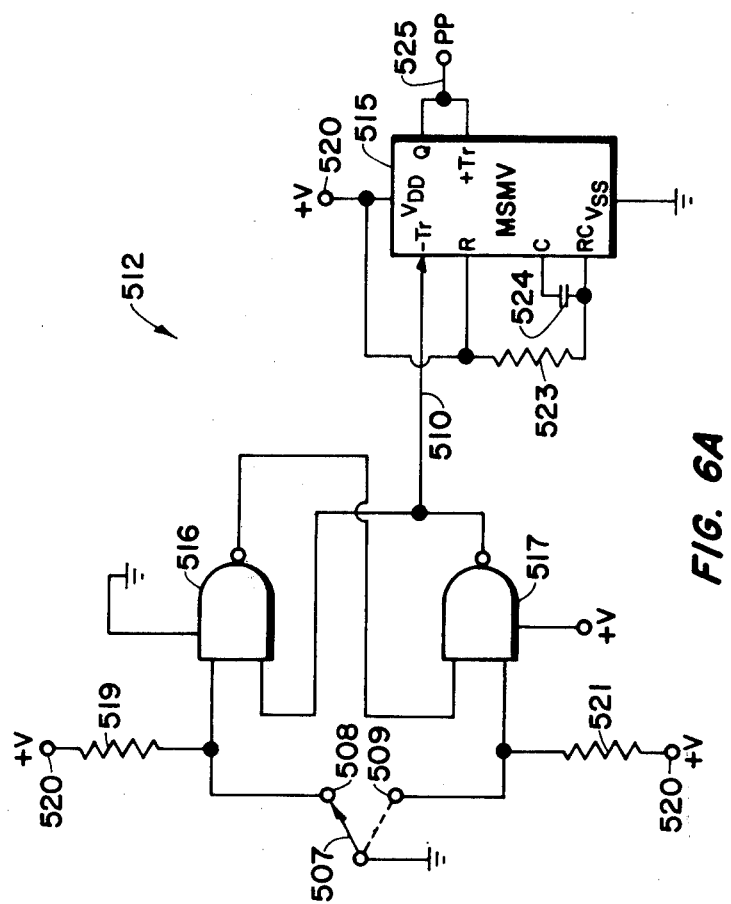
FIGS. 6A, 6B, 6C, and 6D are a detailed electrical schematic diagram of an external control unit for use in transmitting the access and parameter codes to the master parameter control circuit of FIGS. 3A, 3B, and 3C.

More particularly, the clock pulse generator 501 (FIG. 6B) is activated by closing the switch 507 (FIG. 6A). The switch 507, when moved from the upper position 508 to the lower position 509 produces a change from a low to high state upon the output line 510 of an antibounce circuit, generally denoted by the reference numeral 512. Upon the return of the switch 507 to the upper position 508, the state on line 510 changes from high to low, to thereby trigger a monostable multivibrator 515, which, as below described, produces a resetting signal upon the line 525 to the various circuit elements of the control unit and a subsequent start pulse.

The antibounce circuit 512 includes two NAND gates 516 and 517 and the monostable multivibrator 515, which is connected to be non-retriggerable after its initial trigger signal has been received.

One input of the NAND gate 516 is connected via a resistor 519 to a positive terminal 520 to thereby define a normally high state thereupon. This terminal is additionally connected to the upper terminal 508 of the start switch 507. The other input to the NAND gate 516 is connected to the output of the NAND gate 517. In a similar fashion, one input of the NAND gate 517 is connected by a resistor 521 to a positive terminal 520 and also to the lower terminal 509 of the switch 507. The other input of the NAND gate 517 is connected to the output of the NAND gate 516. The output of the NAND gate 517 is the output of the circuit, and is directed to the monostable multivibrator 515.

As shown, the monostable multivibrator 515 is triggered upon a negative going pulse (i.e., a pulse changing from high to low states). Upon the occurrence of such state change, the output Q changes from low to high states, where it remains for a time period depending upon the value of a resistor 523 and a capacitor 524 connected from the RC terminal to the R and C terminals respectively. The R terminal is connected to the positive terminal 520. The positive trigger input is connected to the Q output to provide for the trailing edge (negative going) triggering, non-retriggering capability of the monostable multivibrator 515, as mentioned.

It can thefore be seen that upon the application of a negative going signal upon the trigger input of the multivibrator 515, the Q output changes from low to high states, during which a resetting signal is delivered to the various circuit components upon the line 525, as below described, to provide an initial starting state therefore, After the output Q from the multivibrator 515 has remained in the high state for the time determined by the time constant defined by the capacitor 524 and the resistor 523, it changes in state from high to low. This state change triggers a second monostable multivibrator 527 (FIG. 6B), which procudes a signal to a J-K master-slave flip-flop 528, which serves as a start latch.

The monostable multivibrator 527 is connected in a fashion similar to the monostable multivibrator 515, to be triggered by a negative going pulse applied to the minus trigger input for a time period defined by the RC time constant of the capacitor 530 and resistor 531 connected from the RC terminal to the C and R terminals respectively. Additionally, the R terminals is connected to a positive terminal 520. The positive trigger input is connected to the Q output to provide for the non-triggerable capability of the monostable multivibrator 527.

The J and K inputs of the flip-flop 528 are tied low, together with the clock input. The output from the monostable multivibrator 527 is connected to the set terminal and the output is derived upon the Q terminal. The reset terminal is connected to the output of a pulse generator 532 which produces a pulse upon the completion of the pulse generating sequence of the control unit 500, as below described in detail. The output upon the terminal Q of the flip-flop 528 provides the enable signal upon the line 534 to the clock pulse generator 501.

The clock pulse generator 501 includes a fourteen stage ripple carry binary counter/divider and oscillator 536, a decade counter 537 and three NAND gates 539, 540, and 541. The oscillator/counter 536 and the decade counter 537 each have their reset terminals connected to the reset line 525, above described. The oscillator/-counter 536 has its clock and inverted clock terminals ($\phi$ and $\bar{\phi}$) interconnected by a capacitor 543, a fixed resistor 544 and a variable resistor 545 connected in series. A second fixed resistor 547 is connected between the junction of the capacitor 543 and resistor 544 to one input of the NAND gate 539. The other input of the NAND gate 539 is connected to the output of the start latch flip-flop 528 upon the line 534. The output at $Q_8$ of the oscillator/counter 536 is connected to an inverting NAND gate 540, to provide clock pulses to the access code generator 502, below described. The frequency derived at the terminal $Q_9$ of the oscillator/counter 536 corresponds to the internal clock frequency of the pacer by which the received access and parameter controlling codes are clocked into the various registers. This clock frequency is derived at the $Q_5$ output of the counter 259 (FIG. 3B).

Figure 6B:
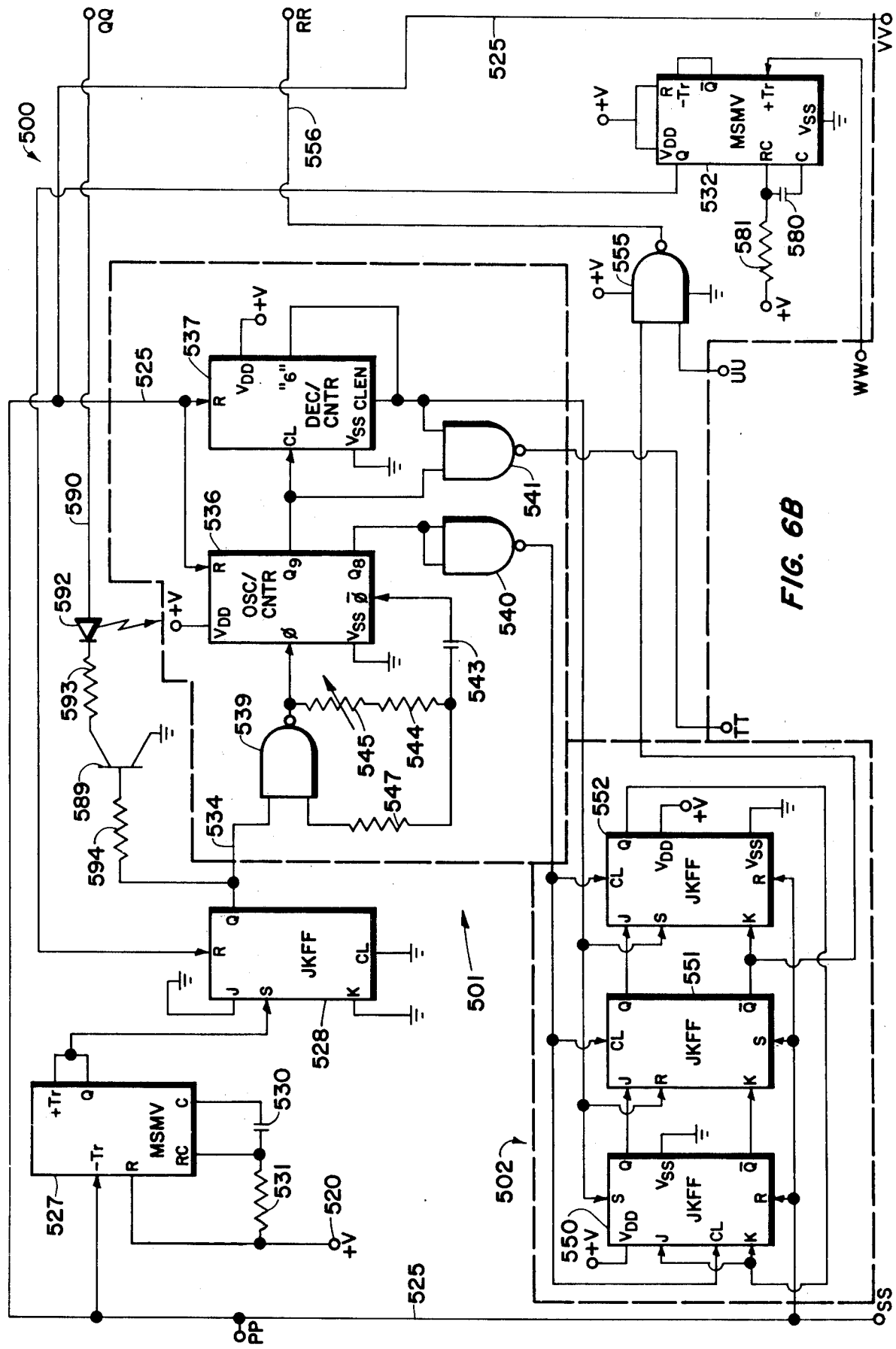
Figure 6C:
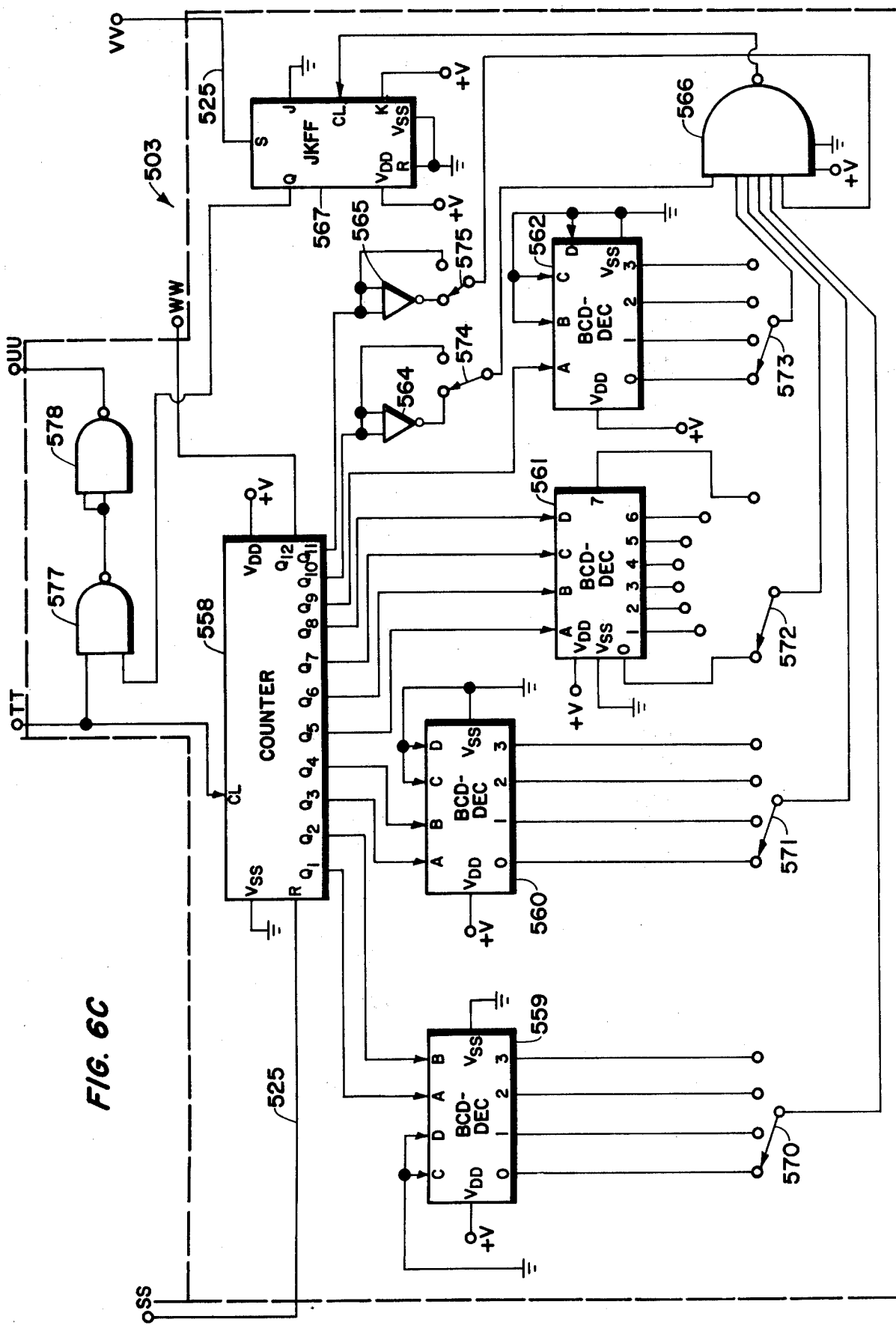

The output upon the terminal $Q_9$ is connected to the clock input of the decade counter 537 and to one input of the NAND gate 541. The output from the NAND gate 541, representing the clock pulses appearing at the $Q_9$ terminal of the oscillator 536, are connected to one input terminal of the NAND gate 577 (FIG. 6C), as well as to the clock input of the counter 558 (FIG. 6C). The output at the "6" terminal of the decade counter 537 is connected to the clock enable input, to thereby inhibit the count of the decade counter 537 after the 6 counter is reached. The output upon the 6 line of the counter 537 is additionally connected to another input of the NAND gate 541 and to the various set and reset terminals of the parameter code generator 503 (FIG. 6C), below described.

In operation, the block pulse generator 501 will produce pulses so long as the signal on the line 534 is in a high state. When, however, the signal on line 534 is low, the clock input to the counter/oscillator 536 cannot vary, thereby stopping the generation of output pulses. The decade counter 537 serves to switch between the access code generator output 502 (FIG. 6B) after the access code has been generated and delivered to the output to the parameter code generator 503 (FIG. 6C) output for its subsequent delivery to the output. This is achieved by the NAND gate 541 which serves to selected between the output of the access code generator and the following parameter code sequence. Thus, prior to the time at which the counter 537 reaches a 6 count, the input to the NAND gate from the 6 output of the counter 537 is in a low state, thereby disabling the passage of the clock pulses upon the line $Q_9$ of the oscillator 536. Therefore, the input of the NAND gate 555 due to the parameter code sequence remains in a high state, allowing only the access code generated by the access code generator 502 to be delivered to the output line 556. Upon the reaching of the 6 count by the counter 537, the clock pulses produced upon the line $Q_9$ of the oscillator 536 are permitted to pass the NAND gate 541, to be delivered to the output line 556 via NAND gates 577, 578 (connected as an inverter), (FIG. 6C) and 555 (FIG. 6B). The high state on the 6 output of the counter 537 produces a reset state continually upon the flip-flop 551 of the access code generator 502, to thereby produce a continuously high state on the $\bar{Q}$ output thereof, to permit the parameter code sequence to pass the NAND gate 555, as below described.

The access code generator 502 includes three J-K master-slave flip-flops 550, 551 and 552. The J and K inputs of the flip-flop 550 are connected to the Q output of the flip-flop 552. The Q and $\bar{Q}$ outputs of the flip-flop 550 are connected, respectively, to the J and K inputs of the flip-flop 551, and the Q and $\bar{Q}$ outputs of the flip-flop 551 are connected, in turn, to the J and K inputs, respectively, of the flip-flop 552. The reset terminals of the flip-flops 550 and 552 as well as the set terminal of the flip-flop 551 are connected to the reset line 525. The set terminals of the flip-flops 550 and 552, as well as the reset terminal of the flip-flop 551 are connected to the 6 output of the decade counter 537. The output from the access code generator circuit is taken from the $\bar{Q}$ terminal of the flip-flop 551. Thus, in operation, the flip-flops 550-552 of the access code generator are initialized by the signal on the reset line 525. Upon the reception of clock pulses from the clock pulse generator 501, and the output $\overline{Q}$ output of the flip-flop 551 will produce the following logic sequence: 1000010 — at a frequency half that of the $Q_8$ output of the oscillator/counter 536 (at the same frequency of $Q_9$).

The $\overline{Q}$ output of the flip-flop 551 is connected to one input of a NAND gate 555. Thus, assuming the other input to the NAND gate 555 is in a high state (which it is until the counter 6 of the decade counter 537 is reached, as will become apparent below), the inverted output upon the line 556 will be: 1000010, which is reinverted by the transmitting coil, below described.

As above described the one shot pulse generator 151 (FIG. 3A) of the master parameter control circuit 150 produces an output pulse only upon a change in input state from low to high. Therefore the code generated by the one shot pulse generator in response to a transmitted digital signal of 01100010 is 1000010. This is the precise code recognized by the access code recognition circuit 270 (FIG. 3B).

The parameter code generator 503 (FIG. 6C) includes a twelve stage ripple carry counter 558, four BCD to decimal decoders 559, 560, 561 and 562, two inverters 564 and 565, a NAND gate 566 capable of comparing at least six inputs and a J-K master-slave flip-flop 567. More particularly, the counter 558 receives clock pulses from the output of the NAND gate 541 (FIG. 6B), being the clock frequency produced by the oscillator 536 divided by $2^9$. The reset terminal is connected to the reset line 525, and the $Q_1$-$Q_{11}$ outputs are connected to the externally controlled parameter selection circuit, below described. The $Q_{12}$ output is connected to a master stop latch 532, as above reference, to stop the oscillator after the completion of the parameter code count. Still more particularly, the $Q_1$ and $Q_2$ outputs of the cunter 558 are connected to the A and B inputs of the BCD to decimal decoder 559. The C and D inputs of the BCD to decimal decoder 559 are connected to a ground terminal to thereby present a low state thereupon. A four position switch 570 has each of its four terminals connected to the 0, 1, 2, and 3 terminals of the BCD to decimal decoder, respectively. The wiper portion of the switch 570 is connected to one of the inputs of the six input NAND gate 566.

The outputs $Q_3$ and $Q_4$ of the counter 558 are connected to the input terminals A and B, respectively, of the BCD to decimal decoder 560. The C and D inputs are connected to a ground or low state. The 0, 1, 2, and 3 outputs of the BCD to decimal decoder 560 are connected to respective terminals of a four position switch 571. The wiper of the switch 571 is connected to another input of the six input NAND gate 566. The output terminals $Q_5$-$Q_8$ of the counter 558 are connected to respective inputs A-D of the BCD to decimal decoder 561. The outputs 0-7 of the BCD to decimal decoder are connected to respectively terminals of a eight position switch 572, the wiper arm of which is also connected to an input of the six input NAND gate 566. The output terminal $Q_9$ of the counter 558 is connected to the A input of the BCD to decimal decoder 562, and the B-D inputs of the BCD to decimal decoder 562 are connected to ground or a low state. The outputs 0-3 of the BCD to decimal decoder 562 are connected to a respective one of a four terminal switch 573, the wiper arm of which is connected to one of the inputs of the six input NAND gate 566. The output $Q_{10}$ of the counter 558 is connected to an input of an inverting NAND gate 564 (shown schematically merely as an inverter), and, to one terminal of a two position switch 574. The output of the inverting NAND gate 564 is connected to the other terminal of the switch 574. The wiper of the switch 574 is connected to another input of the six input NAND gate 566. Finally, the output $Q_{11}$ of the counter 558 is connected to the inputs of an inverting NAND gate 565 (also shown simply as an inverter) and to one terminal of a switch 575. The output of the inverting NAND gate 565 is connected to the other terminal of the two position switch 575. The wiper of the switch 575 is connected to a sixth input of the six input of the NAND gate 566.

The output terminal of the six input NAND gate 566 is connected to the clock terminal of the J-K flip-flop 567. The J and K terminals of the flip-flop 567 are connected to low and high states, respectively, and the output is derived at the Q terminal, which is connected to an input of the NAND gate 577.

The $Q_{12}$ output of the counter 558 is connected to a multivibrator master stop latch 532 (FIG. 6B).

In operation, the various switches 570-575 are set to correspond to a predetermined set of pacer operating parameters. For example, the switch 570, in the embodiment illustrated, represents the sensitivity parameter of the pacer, and can be positioned to correspond to either the 0, 1, 2, or 3 output terminals of the BCD to decimal decoder 559. In a similar fasion, the switches 571, 572, and 573 can be located to respective terminals of the BCD to decimal decoders 560, 561, and 562 to determine the amplitude, rate, and the refractory period of the pacer, as desired. The switches 574 and 575 can be positioned to determine the desired width and operating mode of the pacer. When each of the output terminals $Q_1$-$Q_{11}$ presents a state corresponding to the chosen decimal number (0-3 for switch 570, 0-3 for switch 571, 0-7 for switch 572, 0-3 for switch 562, on or off for switch 574, or on and off for switch 575), all of the inputs to the NAND gate 566 will be in a high state, thereby producing a low state at the output of the NAND gate 566. Concurrently, since the clock pulses upon the clock output terminal $Q_9$ of the oscillator 536 are applied to the output line 556 via NAND gates 577, 578, and 559, the decimal equivalent number of pulses are produced on the output line 556. Upon the occurrence of the next clock pulse, the output states $Q_1$-$Q_{11}$ will be not concurring with the selected parameters as determined by the positions of the respective switches 570-575. The output from the NAND gate 566, therefore, will change from low to high, thereby producing a low state upon the Q terminal of the flip-flop 567. The low state, applied to the NAND gate 577 prevents further transmission of the clock pulses from the output $Q_9$ of the oscillator 536. Therefore, the number of pulses delivered upon the line 556 corresponds to a unique combination or set of desired operating pacer parameters.

When the counter 558 reaches the count to produce a high state upon the output $Q_{12}$, the monostable multivibrator 532 (FIG. 6B) is triggered to produce a resetting signal upon its Q output line, which is delivered to the reset terminal of the start latch flip-flop 528 (FIG. 6B). Upon the occurrence of the resetting signal, the Q output of the flip-flop 528 is changed from high to low states, thereby disabling further operation by the oscillator 536 (FIG. 6B). The monostable multivibrator 532

(FIG. 6B) is connected to trigger upon a positive going pulse, to produce a pulse of width determined by the values of the capacitor 580 and resistor 581 connected between the C and RC terminals and a highstate, as shown. The $\overline{Q}$ output is connected to the negative trigger to produce a non-retriggerable state for triggering upon a positive going edge.

Figure 6D:
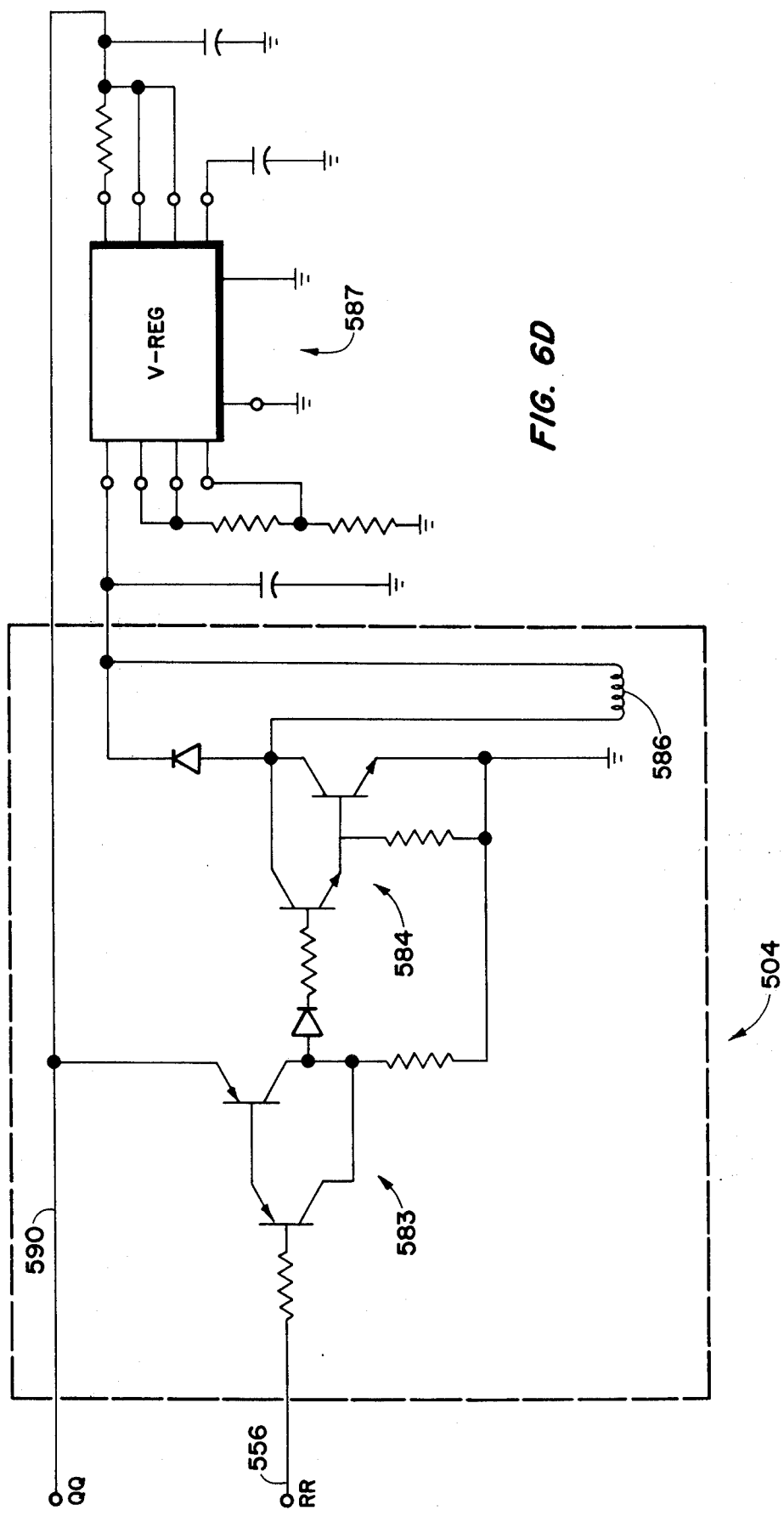

With reference now to FIG. 6D, the access and parameter codes are sequentially delivered upon the line 556 to a pair of Darlington transistor pairs 583 and 584 for amplification and delivery to an electromagnetic field generating coil 586. The voltage to the coil 586 is regulated by a voltage regulator circuit 587, and its associated externally connected components. Thus, in operation, the electromagnetic field generating coil 586 is placed adjacent to the body of the wearer of the pacer circuit 10. Upon the actuation of the start switch 507 (FIG. 6A), the access code and the following parameter code are generated and delivered in sequence to the coil 586, to thereby generate an electromagnetic field in accordance with the sequence. The electromagnetic field is detected upon the reed switch 215 (FIGS. 1 and 3A) to control the pacer 10 in the manner above described.

To assure that the control unit 500 is properly operating, an n-p-n transistor 589 (FIG. 6B) is connected between a positive voltage terminal 590 (which may be derived from the voltage regulator circuit 587, as shown) and ground. A light emitting diode 592 and collector resistor 593 are connected in series between the positive line 590 and the collector of the transistor 589. The emitter of the transistor 589 is connected to a ground potential, and the base of the transistor 589 is connected to the Q output of the flip-flop 528. Thus, when the Q output of the flip-flop 528 changes from low to high states, the base emitter junction of the transistor 589 is forward biased, to thereby permit conduction through the light emitting diode 592 to present a visual indication of the operation of the circuit.

The circuits, above described, can be realized with the following specific components. The components below listed are only set forth by way of example, as other components can be equally advantageously used, as will be apparent to those skilled in the art.

| Integrated Circuits (RCA type) | |
|---|---|
| Component | Number |
| 200 | CD 4047 |
| 203,235,276, 280,402,403, 528,550,551, 552,567 | CD 4027 |
| 204,221,220, 240,241,290, 292,300,301, 384,385 | CD 4013 |
| 15,38,222, 258,259,291, 558 | CD 4040 |
| 165 | CD 4015 |
| 295 | MC 14508 |
| 332 | CA 3093 |
| 333,343,359, 362 | CD 4016 |
| Component | Number |
| 377,391,405 | CD 4051 |
| 515,527,532 | MC 14528 |
| 536 | CD 4060 |
| 537 | CD 4017 |
| 559,560,561, 562 | CD 4028 |
| Gates and Inverters (RCA type) | |
| Component | Number |

-continued

| | | |
|---|---|---|
| 30,40,45, 156,170,174, 358,327,387, 516,517,539, 540,541,555, 564,565,577, 578 | | CD 4011 |
| 216,272,273, 274 | | CD 4069 |
| 180,223,260, 376,390,393, 395,396,397, 398 | | CD 4081 |
| 172,566 | | CD 4068 |
| 356,370,371 | | CD 4007 |
| Transistors | | |
| Component | | Number |
| 356 | | (see gate 356) |
| 310,311,589 | | 2N2222 |
| Diodes | | |
| Component | | Number |
| 213 | | IN 4623 |
| 361 | | 5082-2835 |
| 344,364 | | IN 3070 |
| 324 | | IN 756A |
| Resistors | | |
| Number | | Value |
| 212 | | 2 megohms (variable) |
| 365 | | 3.9 megohms |
| 355 | | 10 megohms |
| 352,519,521 | | 1 megohm |
| 353 | | 400 kilohms |
| 346 | | 22 kilohms |
| 349 | | 6.8 megohms |
| 340 | | 51 kilohms |
| 322 | | 30 kilohms |
| 318,320 | | 4.7 kilohms |
| 326,329 | | 130 kilohms |
| 316,594 | | 10 kilohms |
| 330 | | 68 kilohms |
| 523,531 | | 200 kilohms |
| 593 | | 1 kilohm |
| 547 | | 75 kilohms |
| 544 | | 1.1 kilohms |
| 545 | | 10 kilohms (variable) |
| Capacitors | | |
| Number | | Value |
| 211 | | 100 picofarads |
| 350 | | 50 picofarads |
| 341 | | 0.1 microfarads |
| 347 | | 0.22 microfarads |
| Number | | Value |
| 313,314 | | 39 microfarads |
| 524,530 | | 0.01 microfarads |
| 543 | | 820 picofarads |

Although the invention has been described and illustrated with a certain degree of particularity, it is understood that the present disclosure is made by way of example only, and that numerous changes and modifications in the combination and arrangement of parts may be resorted to without departing from the spirit and scope of the invention as hereinafter claimed.

I claim:

1. An implantable cardiac paces for connection to heart contacting electrodes comprising:
   means for generating a plurality of clock pulses within a normal heartbeat interval;
   triggerable means for generating a heart stimulation pulse for delivery to said heart electrodes;
   means for counting said clock pulses for a stimulation pulse interval to thereafter deliver a trigger signal to said stimulation pulse generating means;
   means for counting said clock pules to a refractory interval count;
   means for detecting signals upon the heart electrodes and for generating a signal in response thereto to reinitiate the count of said refractory interval counting means;

means responsive to said detected heart electrode signal after said refractory interval count for resetting said stimulation counter;

means for independently adjusting the width of said stimulation pulse, the amplitude of said stimulation pulse, the refractory interval count, the stimulation pulse interval, the sensitivity of said detecting means, and the resetting of said stimulation counter;

means for receiving externally transmitted parameter control signals;

register means connected to said receiving means into which said parameter control signals are loaded prior to their execution;

memory means connected to receive signals from said register means for storing said parameter control signals for controlling said independent adjusting means;

means operative to load said parameter control signals into said memory means after said parameter control signals are loaded into said register means;

and means interconnecting said memory means to said adjusting means to execute the parameter control signals in said memory means, whereby said stimulation pulse width, stimulation pulse amplitude, refractory interval count, stimulation pulse interval, sensitivity of said detecting means and resetting of said stimulation counter are controlled by said parameter control signals.

2. The pacer of claim 1 further comprising means for generating a unique parameter determining signal at a location remote from said pacer, said signal uniquely identifying a selectible set of pacer operating parameters;

means for transmitting said signal to said pacer;

and means for receiving said signal in said pacer and generating said sequence of parameter control signals in response thereto for storage in said memory means.

3. The pacer of claim 2 wherein said transmitting means comprises means for generating electromagnetic pulses and wherein said means for receiving said signal in said pacer comprises a magnetically actuated reed switch.

4. The pacer of claim 2 wherein said means for generating a signal comprises means for producing a selectible number of electromagnetic pulses correlating in number to a predetermined unique set of pacer parameters.

5. The pacer of claim 2 further comprising an access code detecting circuit responsive to a predetermined sequence of signals preceding said unique parameter determining signal to enable said control signals to be loaded into said memory.

6. The pacer of claim 5 wherein said access code detecting circuit is responsive only to a predetermined access sequence of signals at a particular frequency.

7. The pacer of claim 6 wherein said access code comprises both high and low logic states.

8. The pacer of claim 2 wherein said means for generating said parameter determining signal comprises a clock pulse generator and means responsive to the clock pulses for spacing said parameter determining signals, and wherein said pacer includes a clock pulse responsive means to control the reception of said parameter determining signals at a comparable clock frequency.

9. An implantable digital cardiac pacer adapted to deliver stimulation pulses to a heart contacting electrode having externally selectible operating parameters comprising:

a heart stimulation pulse generator for connection to said electrode;

an external instruction device adapted to transmit a train of parameter selection pulses;

means for receiving said train of pulses and for generating a digital signal in response thereto;

memory means for storing said digital signal;

means interconnecting said pulse receiving means and said memory means to permit the loading of said digital signal into said memory means only after said train of pulses is entirely received by said receiving means;

means for varying at least one of the operating parameters of said pulse generator;

and means connecting said memory means and said parameter varying means to enable said parameter varying means to control said at least one operating parameter in response to said digital signal.

10. The pacer of claim 9 further comprising means within said external instruction device for generating an access code signal preceding said train of parameter selection pulses, and wherein said means to control the loading of said digital signal into said memory means further comprises unlatching circuitry means adapted to discriminatingly reject all external signals until said access code has been recognized.

11. The pacer of claim 10 wherein said train of said parameter selection pulses and said access code signal comprise electromagnetic pulses generated by said external instruction device.

12. The pacer of claim 11 wherein said instruction device transmits said electromagnetic pulses at a predetermined frequency, and wherein said receiving means comprises a magnetically responsive reed switch within said pacer to receive said electromagnetic pulses, and further comprising means within said pacer for constraining the loading of said memory means only to said digital signal when generated in response to said electromagnetic pulses of said predetermined frequency.

13. A heart pacer having a pulse generator for delivering stimulation pulses to a heart contacting electrode and having selectible discrete operating parameters, comprising:

means for receiving a train of pulses of number corresponding to a preassigned pacer parameter combination;

means for counting the pulses received to produce a binary signal representing the number of said pulses in said train;

memory means into which said binary signal is loaded;

counting means connected to said memory means to permit said binary signal to be loaded into said memory only after the train of pulses is entirely received;

and control means connected to said memory means to select said operating parameters in said preassigned parameter combination for controlling said pulse generator.

14. The heart pacer of claim 13 further comprising a pulse transmitter for generating a train of pulses at a location remote from the pacer, the number of pulses being selectible to correspond to a preassigned pacer parameter combination.

15. The heart pacer of claim 14 wherein said pulse transmitter generates a train of electromagnetic pulses, and wherein said means for receiving a train of pulses comprises an electromagnetically actuated reed switch.

16. The heart pacer of claim 13 further comprising means connected to said electrode to detect pulses thereon to inhibit said pulse generator in response thereto and means connected to said pacer to control the asynchronous pulse rate, pulse amplitude, and pulse width of said pulse generator and the sensitivity, refractory period and mode of said inhibit means in response to said control means.

17. The heart pacer of claim 13 further comprising latch means to which said train of pulses is applied for disabling said binary signal producing counting means until said latch means receives a predetermined access sequence of pulse.

18. The heart pacer of claim 17 wherein said latch means comprises access recognition circuit means for recognizing a predetermined access code having at least one inverted pulse.

19. For use in a digital heart pacer of the type which receives externally transmitted pulses, a "one shot" digital pulse generator for producing a pulse of controlled amplitude and width upon the application of said received pulse, comprising:
a source of digital "high" and "low" states;
a clock pulse generator;
first and second flip-flop means each having a data input terminal, an output terminal, an inverted output terminal, a clock terminal operable to produce a next state output in accordance with the present state input, and a reset terminal;
said received pulse being conducted to the clock input of said first flip-flop, said data input terminal of said first flip-flop being connected to a digital "high" state, and the output of said first flip-flop being connected to the data input of said second flip-flop, and additionally defining the output of said digital "one shot" generator;
counter means having a clock input and an output which changes state after the application of a predetermined number of clock pulses to the clock input, and a reset terminal to initialize said counter;
said counter being reset by the signal on the inverted output terminal of said first flip-flop, and providing a signal upon said output terminal to said clock terminal of said second flip-flop, said counter receiving clock pulses from a clock generator upon its clock input terminal;
the output from said second flip-flop being connected to reset said first and second flip-flops to an initial state;
whereby upon the application of a received pulse to said first flip-flop, an output is presented upon its output terminals which is of predetermined amplitude, continuing until said first and second flip-flops are reset as controlled by the count output of said counter.

20. A circuit for controlling the parameters of an implantable cardiac pacer responsive to remote signals having a first portion defining an access code having both high and low logic states, and a second portion defining a parameter controlling code comprising,
means for receiving said remote signals,
access code recognizing circuit means for signalling the reception of said access code having both high and low logic states,
means for counting said second portion of said remote signals to produce a digital representation thereof,
gate means receiving said second portion for passing said second portion only after said access code recognizing circuit signals reception of said access code,
storage means for loading thereinto said digital representation of said second portion from said counting means for controlling the pacer parameters,
means for controlling the pacer parameters in accordance with said parameter controlling code in response to said digital representation loaded into said storage means.

21. The circuit of claim 20 further comprising timing means including clock means for generating timing pulses, and second gate means connected to receive said timing pulses and said remote signals to pass said remote signals to said second portion receiving gate means and said access code recognizing circuit means only in conjunction with said timing pulses.

22. The circuit of claim 21 further comprising means for timing the reception of said second portion to only thereafter permit said digital representation to be loaded into said storage means.

23. The circuit of claim 20 further comprising means for timing the reception of said second portion to only thereafter permit said digital representation to be loaded into said storage means.

24. A circuit for controlling after the reception of a cardiac signal or a stimulation signal the refractory period of an implantable digital cardiac pacer having a resettable stimulation pulse interval controlling means comprising:
means for producing a first reset signal upon detecting a cardiac or a stimulation signal,
a source of clock pulses,
a counter resettable by said first reset signal for counting said clock pulses after the occurrence of said first reset signal to produce at least first and second output signals at predetermined clock pulse counts,
signal selection means responsive to a digital signal applied to an input thereof and having inputs to which said first and second output signals are applied to produce a selected signal determined by said digital signal,
means for generating said digital signal in response to a remotely generated control signal, and
means to produce a second reset signal for resetting said stimulation pulse interval controlling means, said resetting signal producing means being enabled by said selected signal to thereafter produce said second signal upon the reception of a next following first reset signal.

* * * * *